US008105608B2

(12) United States Patent
Low et al.

(10) Patent No.: US 8,105,608 B2
(45) Date of Patent: *Jan. 31, 2012

(54) METHOD OF TREATMENT USING LIGAND-IMMUNOGEN CONJUGATES

(75) Inventors: Philip Stewart Low, West Lafayette, IN (US); Yingjuan Lu, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1174 days.

This patent is subject to a terminal disclaimer.

(21) Appl. No.: 11/274,973

(22) Filed: Nov. 16, 2005

(65) Prior Publication Data

US 2006/0067946 A1  Mar. 30, 2006

Related U.S. Application Data

(63) Continuation of application No. 09/822,379, filed on Mar. 30, 2001, now Pat. No. 7,033,594.

(60) Provisional application No. 60/193,944, filed on Mar. 31, 2000, provisional application No. 60/255,846, filed on Dec. 15, 2000.

(51) Int. Cl.
*A61K 39/00* (2006.01)
*A61K 31/495* (2006.01)
*A61K 31/445* (2006.01)
*A61K 31/50* (2006.01)
*A61K 31/34* (2006.01)

(52) U.S. Cl. .......... 424/193.1; 424/194.1; 424/85.1; 424/85.2; 424/85.5; 424/85.7; 514/294; 514/253; 514/255; 514/258

(58) Field of Classification Search .......... None
See application file for complete search history.

(56) References Cited

U.S. PATENT DOCUMENTS

| | | | |
|---|---|---|---|
| 2,816,110 A | | 12/1957 | Sletzinger et al. |
| 4,314,988 A | | 2/1982 | Farina et al. |
| 4,659,655 A | * | 4/1987 | Rose ............... 435/7.21 |
| 4,675,382 A | | 6/1987 | Murphy |
| 4,676,980 A | | 6/1987 | Segal et al. |
| 4,681,760 A | | 7/1987 | Fathman |
| 4,713,249 A | | 12/1987 | Schroder |
| 4,946,945 A | | 8/1990 | Wojdani |
| 4,971,792 A | | 11/1990 | Steplewski et al. |
| 5,057,540 A | | 10/1991 | Kensil et al. |
| 5,075,287 A | | 12/1991 | Hasegawa |
| 5,108,921 A | | 4/1992 | Low et al. |
| 5,117,022 A | * | 5/1992 | Khokhar et al. .............. 556/137 |
| 5,137,720 A | | 8/1992 | Gangemi et al. |
| 5,140,104 A | | 8/1992 | Coughlin et al. |
| 5,266,333 A | | 11/1993 | Cady et al. |
| 5,273,965 A | | 12/1993 | Kensil et al. |
| 5,298,395 A | | 3/1994 | Park |
| 5,416,016 A | | 5/1995 | Low et al. |
| 5,417,982 A | | 5/1995 | Modi |
| 5,443,829 A | | 8/1995 | Kensil et al. |
| 5,508,310 A | | 4/1996 | Rhodes |
| 5,547,668 A | | 8/1996 | Kranz et al. |
| 5,552,545 A | | 9/1996 | Pearce et al. |
| 5,583,112 A | | 12/1996 | Kensil et al. |
| 5,583,202 A | | 12/1996 | Zanetti |
| 5,602,171 A | * | 2/1997 | Tang et al. ................ 514/455 |
| 5,635,382 A | | 6/1997 | Low et al. |
| 5,650,398 A | | 7/1997 | Kensil et al. |
| 5,672,486 A | | 9/1997 | Soulillou |
| 5,688,488 A | | 11/1997 | Low et al. |
| 5,747,024 A | | 5/1998 | Grabstein et al. |
| 5,820,847 A | | 10/1998 | Low et al. |
| 5,932,208 A | | 8/1999 | Chedid et al. |
| 5,977,081 A | | 11/1999 | Marciani |
| 6,080,725 A | | 6/2000 | Marciani |
| 6,231,859 B1 | | 5/2001 | Kensil |
| 6,262,029 B1 | | 7/2001 | Press et al. |
| 6,291,673 B1 | | 9/2001 | Fuchs et al. |
| 6,335,434 B1 | | 1/2002 | Guzaev et al. |
| 7,033,594 B2 | | 4/2006 | Low et al. |
| 7,601,332 B2 | | 10/2009 | Vlahov et al. |
| 2001/0031252 A1 | | 10/2001 | Low et al. |
| 2002/0039583 A1 | | 4/2002 | Subjeck et al. |
| 2003/0086900 A1 | | 5/2003 | Low et al. |

(Continued)

FOREIGN PATENT DOCUMENTS

EP   0180171   5/1986

(Continued)

OTHER PUBLICATIONS

Wang et al (Bioconjugate Chemistry, 1997, vol. 8, pp. 673-679).*

(Continued)

*Primary Examiner* — Karen A Canella
(74) *Attorney, Agent, or Firm* — Barnes & Thornburg LLP

(57) ABSTRACT

A method and pharmaceutical composition are provided for enhancing the endogenous immune response-mediated elimination of a population of pathogenic cells in a host animal wherein the pathogenic cells preferentially express, uniquely express, or overexpress a binding site for a particular ligand. The invention comprises administering the ligand conjugated to an immunogen to a host animal harboring the population of pathogenic cells. Antibodies, preexisting or administered to the host animal to establish a passive immunity, directed against the immunogen bind to the ligand-immunogen conjugate resulting in elimination of the pathogenic cells by the host's immune response. At least one additional therapeutic factor is administered selected from the group consisting of a cell killing agent, a tumor penetration enhancer, a chemotherapeutic agent, antimicrobial agent, a cytotoxic immune cell, and a compound capable of stimulating an endogenous immune response wherein the compound does not bind to the ligand-immunogen conjugate.

36 Claims, 17 Drawing Sheets

U.S. PATENT DOCUMENTS

| | | | |
|---|---|---|---|
| 2003/0198643 | A1 | 10/2003 | Lu |
| 2006/0002891 | A1 | 1/2006 | Pouletty |
| 2006/0067946 | A1 | 3/2006 | Low et al. |
| 2007/0037764 | A1 | 2/2007 | Mourich et al. |
| 2008/0317706 | A1 | 12/2008 | Low et al. |

FOREIGN PATENT DOCUMENTS

| | | |
|---|---|---|
| EP | 0220030 A2 | 4/1987 |
| EP | 217577 | 8/1987 |
| EP | 0 305 967 | 3/1989 |
| EP | 0 324 625 | 7/1989 |
| EP | 0334300 | 9/1989 |
| EP | 0352761 | 1/1990 |
| EP | 0 367 166 | 5/1990 |
| EP | 0 369 387 | 5/1990 |
| EP | 0 510 949 | 10/1992 |
| JP | 64-79125 | 3/1989 |
| JP | 3-48766 | 7/1989 |
| JP | 2-169521 | 6/1990 |
| JP | 3-173814 | 7/1991 |
| JP | 7-173071 | 4/1992 |
| JP | 7-303499 | 11/1995 |
| WO | WO 85/04808 | 11/1985 |
| WO | WO 88/03566 | 5/1988 |
| WO | WO 90/11779 | 10/1990 |
| WO | WO 91/01004 | 1/1991 |
| WO | 9101146 | 2/1991 |
| WO | 9107418 | 5/1991 |
| WO | WO 92/03569 | 3/1992 |
| WO | WO 92/19775 | 11/1992 |
| WO | WO 93/17699 | 9/1993 |
| WO | WO 94/11738 | 5/1994 |
| WO | WO 94/23759 | 10/1994 |
| WO | WO 95/02397 | 1/1995 |
| WO | WO 95/07995 | 3/1995 |
| WO | WO 95/34321 | 12/1995 |
| WO | 9636367 | 11/1996 |
| WO | WO 96/35443 | 11/1996 |
| WO | WO 97/24140 | 7/1997 |
| WO | 9737690 | 10/1997 |
| WO | 9741831 | 11/1997 |
| WO | 0010599 | 3/2000 |
| WO | WO 00/74721 | 12/2000 |
| WO | WO 01/12172 | 2/2001 |
| WO | WO 01/12840 | 2/2001 |
| WO | WO 01/22972 | 4/2001 |
| WO | WO 01/22990 | 4/2001 |
| WO | 0132207 | 5/2001 |
| WO | WO 01/47552 | 7/2001 |
| WO | WO 01/51083 | 7/2001 |
| WO | WO 01/74382 | 10/2001 |

OTHER PUBLICATIONS

George et al., "Redirection of T cell-mediated cytotoxicity by a recombinant single-chain Fv molecule", Journal of Immunology, 152: 1802-1811 (1994).
Berd et al., "Immunization with haptenized, autologous tumor cells induces inflammation of human melanoma metastases", Cancer Research, 51: 2731-2734 (1991).
Link Jr. et al., "Eliciting hyperacute xenograft response to treat human cancer: a(1,3) galatosyltransferase gene therapy," Anticancer Research, 18: 2301-2308 (1998).
Ben-Efraim et al., "Use of xenogenized tumor cells for treatment in experimental tumor and in human neoplasia", Biomed. & Pharmacother, 54: 268-273 (2000).
Olsnes et al., "Immunotoxins Entry into cells and mechanisms of action," Immunology Today, 10(9): 291 (1989).
Melby et al., "Entry of protein toxins in polarized epithelial cells", Cancer Research, 53: 1755 1760 (1993).
Lussow et al., "Redirecting circulating antibodies via ligand hapten conjugates eliminates target cells in vivo", Journal of Immunotherapy, 19(4):257 265 (1996).
Lussow et al., "Targeting of antihapten antibodies to activated T cells via an IL 2 hapten conjugate prolongs cardiac graft survival", Transplantation, 62(12): 1703 1708 (1996).
Roy et al., "Targeting T cells against brain tumors with a bispecific ligand antibody conjugate", Int J. Cancer, 76: 761 766 (1998).
Patrick, et al., "Intracerebral bispecific ligand antibody conjugate increases survival of animals bearing endogenously arising brain tumors", Int. J. Cancer, 78: 470 479 (1998).
Philip Livingston,De Vita, V.T., "Section 23.5: Immunization with synthetic or highly purified tumor antigens," Biologic Therapy of Cancer, 2d ed. Philadelphia, Lippincott, 1995, pp. 680 687.
Guyre et al., "Increased potency of Fc-receptor-targeted antigens", Cancer Immunol. Immunotherapy, 45: 146-149 (1997).
Lanza et al., Use of antigenized antibodies containing CD4 sequences to generate antibodies able to inhibit syncytia formation, FASEB J., Abstract No. 2690, p. A1400 (1992).
K. Hasegawa et al., Composite Immunological Antibiotic (Abstract of CN 1044781C), published Aug. 22, 1990.
Abstract of Easty et al., International Journal of Cancer, 84: 494-501 (1999).
Abstract of Walker-Daniels et al., Prostate, 41: 275-280 (1999).
Abstract of Leamon et al., Journal of Drug Targeting, 7: 157-169 (1999).
Abstract of Mazzoni et al., Proc. Annu. Meet. Am. Assoc. Cancer Res., 38: A558 (1997).
Roberts et al., "Folic acid analogs. Modifications in the benzene-ring region. 3. Neohomofolic and neobishomofolic acids. Improved synthesis of folic acid and its analogs", Journal of Medical Chemistry, 16: 697-699 (1973).
Roberts et al., "Folic acid analogs. Modifications in the benzene-ring region. 2. Thiazole analogs", Journal of Medical Chemistry, 15: 1310-1312 (1972).
Weinstock et al., "Folic acid analogs. II. p-{[(2,6-Diamino-8-purinyl)methyl]amino}-benzoyl-L-glutamic acid and related compounds", Journal of Medical Chemistry, 13: 995-997 (1970).
Drummond et al., "Liposome targeting to tumors using vitamin and growth factor receptors", Vitamins and Hormones, 60: 285-332 (2000).
Insel, "Potential alterations in immunogenicity by combining or simultaneously administering vaccine components", Annals of the New York Academy of Science, 754: 35-47 (1995).
Bock et al., "Sulfonamide structure-activity relations in a cell-free system. 2. Proof for the formation of a sulfonamide-containing folate analog", Journal of Medical Chemistry, 17:23-28 (1974).
Roberts et al., "Folic acid analogs. Modifications in the benzene-ring region. 4. 3'-Ethyl- and 3'-isopropylfolic acids", Journal of Medical Chemistry, 17: 219-222 (1974).
Lee et al., "Folic acid antagonists. Methotrexate analogs containing spurious amino acids. Dichlorohomofolic acid", Journal of Medical Chemistry, 17: 326-330 (1974).
Kim et al., "Synthesis and biological activity of 10-thia-10-deaza analogs of folic acid, pteroic acid, and related compounds", Journal of Medical Chemistry, 18: 776-780 (1975).
Nair et al., "Folate analogues altered in the C9-N10 bridge region. 10-Oxafolic acid and 10-oxaaminopterin", Journal of Medical Chemistry, 19: 825-829 (1976).
Plante et al., "Polyglutamyl and polylysyl derivatives of the lysine analogs of folic acid and homofolic acid", Journal of Medical Chemistry, 19: 1295-1299 (1976).
Hynes et al., "Quinazolines as inhibitors of dihydrofolate reductase. 4. Classical analogs of folic and isofolic acids", Journal of Medical Chemistry, 20: 588-591 (1977).
Oatis et al., "Synthesis of quinazoline analogs of folic acid modified at position 10", Journal of Medical Chemistry, 20: 1393-1396 (1977).
Nair et al., "Folate analogs altered in the C9-N10 bridge region: N10-tosylisohomofolic acid and N10-tosylisohomoaminopterin", Journal of Medical Chemistry, 21: 673-677 (1978).
Nair et al., "Folate analogs altered in the C9-N10 bridge region: 11-thiohomofolic acid", Journal of Medical Chemistry, 22: 850-858 (1979).
Nair et al., "Folate analogs altered in the C9-N10 bridge region. 14. 11-Oxahomofolic acid, a potential antitumor agent", Journal of Medical Chemistry, 23: 59-65 (1980).

Nair et al., "Folate analogs altered in the C9-N10 bridge region. 18. Synthesis and antitumor evaluation of 11-oxahomoaminopterin and related compounds", Journal of Medical Chemistry, 24: 1068-1073 (1981).

Temple et al., "Synthesis of pseudocofactor analogs as potential inhibitors of the folate enzymes", Journal of Medical Chemistry, 25: 161-166 (1982).

Nair et al., "Folate analogs. 20. Synthesis and antifolate activity of 1',2',3',4',5',6'-hexahydrohomofolic acid", Journal of Medical Chemistry, 26: 135-140 (1983).

Nair et al., "Folate analogs. 21. Synthesis and antifolate and antitumor activities of N10-(cyanomethyl)-5,8-dideazafolic acid", Journal of Medical Chemistry, 26: 605-607 (1983).

Nair et al., "Folate analogs. 22. Synthesis and biological evaluation of two analogs of dihydrofolic acid possessing a 7,8-dihydro-8-oxapterin ring system", Journal of Medical Chemistry, 26: 1164-1198 (1983).

Leamon et al. "Selective targeting of malignant cells with cytotoxin-folate conjugates," J. of Drug Targeting, 2: 101-12 (1994).

Reddy et al., "Expression and functional characterization of the -isoform of the folate receptor on CD34+ cells," Blood, 93: 3940-3948 (1999).

Reddy et al., "Folate-Mediated Targeting of Therapeutic and Imaging Agents to Cancers," Critical Reviews in Therapeutic Drug Carrier Systems, 15(6), 587-627 (1998).

Kranz et al., "Conjugates of folate and anti-T-cell-receptor antibodies specifically target folate-receptor-positive tumor cells for lysis," Proc. Natl. Acad. Sci. USA, vol. 92, pp. 9057-9061, Sep. 1995.

Cho et al., "Single-Chain Fv/Folate Conjugates Mediate Efficient Lysis of Folate-Receptor-Positive Tumor Cells," Bioconjugate Chem., vol. 8, 338-346 (1997).

Ward et al., "Folic Acid Targeting of Protein Conjugates into Ascites Tumour Cells from Ovarian Cancer Patients," Journal of Drug Targeting, vol. 8, No. 2, 119-123 (2000).

Mastrangelo et al., "Active Specific Immunization in the Treatment of Patients With Melanoma," Seminars in Oncology, vol. 23, No. 6, 773-781 (Dec. 1996).

Rihova et al., "Polymeric drugs based on conjugates of synthetic and natural macromolecules. II. Anti-cancer activity of antibody or (Fab')2-targeted conjugates and combined therapy with immunomodulators," Journal of Controlled Release, 64, 241-261 (2000).

Blanka Rihova, "Receptor-mediated targeted drug or toxin delivery," Advanced Drug Delivery Reviews, 29, 273-289 (1998).

Richard A. Insel, "Potential Alterations in Immunogenicity by Combining or Simultaneously Administering Vaccine Components," Annals New York Academy of Sciences, 35-47 (1995).

Roberts et al., "Folic acid analogs. Modifications in the benzene-ring region. 1. 2'- and 3'-Azafolic acids", Journal of Medical Chemistry, 14: 125-130 (1971).

U.S. Appl. No. 60/988,621, filed Nov. 16, 2007, Leamon et al.
U.S. Appl. No. 60/990,815, filed Nov. 28, 2007, Leamon et al.
U.S. Appl. No. 61/003,212, filed Nov. 15, 2007, Leamon et al.
U.S. Appl. No. 61/043,833, filed Apr. 10, 2008, Leamon et al.

Kensil, "Saponins as Vaccine Adjuvants," *Critical reviews in Therapeutic Drug Carrier Systems*, 1996; 13:1-55.

Gridley et al., "Low-dose/low-dose-rate radiation: a feasible strategy to improve cancer radiotherapy?," *Cancer Therapy*, 2005; 3:105-130.

Demaria et al., "Combining Radiotherapy and Immunotherapy: A Revived Partnership," *Int. J. Radiation Oncology Biol. Phys.*, 2005; 63(3):655-666.

Kim et al., "Comparison of the effect of different immunological adjuvants on the antibody and T-cell response to immunization with MUC1-KLH and GD3-KLH conjugate cancer vaccines," Vaccine, vol. 18, 2000, pp. 597-603, XP000999516.

Pisetsky, "Immune Activation by Bacterial DNA: A New Genetic Code," Immunity, vol. 5, 303-310, Oct. 1996.

Database Medline on STN, US National Library of Medicine, No. 2000143207, C. P. Leamon et al., "Folate-Mediated Drug Delivery: Effect of Alternative Conjugation Chemistry," Abstract, Journal of Drug Targeting, 1999, vol. 7, No. 3, pp. 157-169.

Database Medline on STN, US National Library of Medicine, No. 1979:551180, Strominger et al., "Drug-Receptor Interactions: The Example of β-Lactam Antibodies," Abstract, Adv. Pharmacol. Ther. Proc. Int. Congr. Pharmacol., 1979, vol. 10, pp. 209-223.

Database Medline on STN, US National Library of Medicine, No. 1999434114, D.J. Easty et al., "Up-Regulation of Ephrin-A1 During Melanoma Progression," Abstract, International Journal of Cancer, Oct. 22, 1999, vol. 84, No. 5, pp. 494-501.

Database Medline on STN, US National Library of Medicine, No. 2000013158, J. Walker-Daniels et al., "Overexpression of the EphA2 Tyrosine Kinase in Prostate Cancer," Abstract, Prostate, Dec. 1, 1999, vol. 41, No. 4, pp. 275-280.

Database Medline on STN, US National Library of Medicine, No. 2001:267809; S. Kremlev et al., "Macrophage-Mediated Inflammation in Experimental Autoimmune Neuritis: The Role of the Integrin and Cheomkine Interaction," Abstract, FASEB Journal, Mar. 7, 2001, vol. 15, No. 4, p. A682.

Database Medline on STN, US National Library of Medicine, No. 89271983, T. Hamaoka, "Future Perspectives on Tumor-Specific Immunotherapy Using Hapten-Reactive T Cell Activity," Abstract, Gan to Kagaku Ryoho, Apr. 1989, vol. 16, pp. 886-896.

Mazzoni et al., "Immunotherapy of ovarian cancer with ani-CD3/antitumor bi-mAB: Improvement via CD28 costimulation", Abstract, Proc. Annu. Meet. Am. Assoc. Cancer Res., 38: A558 (1997).

Midoux et al., "Activation of Mouse Macrophages by Muramyl Dipeptide Coupled with an Anti-Macrophage Monoclonal Antibody," *Bioconjugate Chem.*, 3:194-199 (1992).

Vidal et al., "Macrophage Stimulation with Murabutide, an HIV-Suppressive Muramyl Peptide Derivative, Selectively Activates Extracellular Signal-Regulated Kinases 1 And 2, C/EBPβ and STAT1: Role of CD14 and Toll-like receptors 2 and 4," *Eur. J. Immunol.*, 31:1962-1971 (2001).

Aderem & Ulevitch, "Toll-like Receptors in the Induction of the Innate Immune Response," *Nature*, 406:782-787 (2000).

Park & Bendelac, "CD1-Restricted T-Cell Responses and Microbial Infection," *Nature*, 406:788-792 (2000).

Akira et al., "Toll-like Receptors: Critical proteins linking innate and acquired immunity," *Nature Immunology*, 2:675-680 (2001).

Low, Philip S., Lu, Yinguan; "Folate-mediated targeting of imaging and immunothcrapeutic agents to tumors in vivo," Proceedings of the American Association for Cancer Research Annual Meeting, vol. 43, Mar. 2002, Abstract 4692, pp. 947-948 (XP002347730).

Low, Philip S. et al., "Folate-Mediated Delivery of Therapeutic and Imaging Agents to Cancer Tissue in vivo," British Journal of Pharmacology, vol. 134, Nov. 2001, p. 178P.

Lu, Yinguan; Low, Philip S.; "Folate targeting of haptens to cancer cell surfaces mediates immunotherapy of syngeneic murine tumors," Cancer Immunology Immunotherapy, vol. 51, 2002, 153-162 (XP-002347729).

Scott et al., "Anti-CD3 Antibody Induces Rapid Expression of Cytokine Genes In Vivo", J. Immunology, 1990, vol. 145(7): 2183-2188.

"Relative Adjuvant Efficacy of Aluminum Hydroxide and Saponin is Related to the Immunogenicity of the antigen," (abstract) Database CAPLUS, Wellcome Res. Lab, R. Bomford, Accession No. 1984:628230; *International Archives of Allergy and Applied Immunology*, 1984 vol. 75(3), pp. 280-281.

Kim, Soo Kie et al.; "Effect of immunological adjuvant combinations on the antibody and T-cell response to vaccination with MUC1-KLH and GD3-KLH conjugates", Vaccine; vol. 19, 2001; pp. 530-537; XP-002385945; ISSN: 0264-410X.

Behboudi et al., "Isolation and quantification of *Quillaja saponaria Molina* saponins and lipids in iscom-matrix and iscoms," Vaccine, 13, 1690-1696 (1995).

Hartmann et al., "CpG DNA: a potent signal for growth, activation, and maturation of human dendritic cells," PNAS, 96, 9305-9310 (1999).

Lu Yingjuan and Low, Philip S., "Targeted immunotherapy of cancer: development of antibody-induced cellular immunity," Journal of Pharmacy and Pharmacology, Feb. 2003, vol. 55, No. 2, pp. 163-167; XP008042814; ISSN: 0022-3573.

May, Richard D. et al., "Preclinical Cancer Vaccine Studies in Mice Using a HER-2 Peptide Immunogen Combined with the Saponin-Based Immune Enhancer GPI-0100 and Polysaccharides," FASEB Journal, vol. 16, No. 4, Mar. 20, 2002, p. A333, XP008065376 &

Annual Meeting of the Professional Reserch Scientists on Experimental Biology; New Orleans, Louisiana, USA; Apr. 20-24, 2002 ISSN: 0892-6638, p. A333, abstract 246.7.

International Search Report/Written Opinion for PCT/US2001/10254 completed Jun. 29, 2001.

Lu et al., "Folate-Mediated Delivery of Macromolecular Anticancer Therapeutic Agents," Advanced Drug Delivery Reviews, vol. 54 (2002), pp. 675-693.

Chu et al., "CpG oligodeoxynucleotides act as adjuvants that switch on T helper 1 (Th1) immunity," J. Exp. Med., 186, pp. 1623-1631 (1997).

Infante-Duarte et al., "Th1 /Th2 balance in infection," Springer Semin Tmmunopathol., 21, 317-338 (1999).

Sakaguchi et al., "Regulatory T cells and immune tolerance," Cell, 133, pp. 775-787 (2008).

Schwartz, "Natural regulatory T cells and self-tolerance," Nature Immunology, 6, pp. 327-330 (2005).

Harris et al., "Shifts from IgG-2 class to IgG-1 class in CBA and C3H anti-BALB/c antibody," Abstract, Transplantation, 19, pp. 318-325 (1975).

Kennedy, Michael D., et al., "Evaluation Of Folate Conjugate Uptake And Transport By The Choroid Plexus Of Mice", May 2003, Pharmaceutical Research, vol. 20, No. 5, pp. 714-719.

Mirzaie-Joniani, Homa, et al., "Apoptosis Induced by Low-Dose and Low-Dose-Rate Radiation", Supplement to Cancer: Eighth Conference on Radioimmunodetection and Radioimmunotherapy for Cancer, American Cancer Society, 2002, pp. 1210-1214.

Sega, Emanuela I., et al., "Low-Dose Radiation Potentiates the Therapeutic Efficacy of Folate Receptor-Targeted Hapten Therapy", International Journal Radiation Oncology, Biology, Physics, 2008, vol. 71, No. 2, pp. 559-566.

Azuma et al., "Development of immunoadjuvants for immunotherapy of cancer", International Immunopharmacology, 1, pp. 1249-1259 (2001).

Takeuchi et al., "Toll-like receptors; their physiological role and signal transduction system", International Immunopharmacology, 1, pp. 625-635 (2001).

Mcans et al., "Structure and function of Toll-like receptor proteins", Life Sciences, 68, pp. 241-258 (2000).

Strominger et al., "Drug-Receptor Interactions: The Example of β-Lactam Antibiotics", Adv. Pharmacol. Ther. Proc. Int. Congr. Pharmacol., 1979, vol. 10, pp. 209-223.

Easty et al., "Up-Regulation of Ephrin-A1 During Melanoma Progression", Int. J. Cancer (Pred. Oncol.): 84, 494-501 (1999).

Nakashima-Matsushita et al., "Selective Expression of Folate Receptor β and Its Possible Role in Methotrexate Transport in Synovial Macrophages from Patients with Rheumatoid Arthritis", Arthritis & Rheumatism, vol. 42, No. 8, Aug. 1999, pp. 1609-1616.

Brightbill et al., "Host Defense Mechanisms Triggered by Microbial Lipoproteins Through Toll-Like Receptors", Science, vol. 285, Jul. 30, 1999, pp. 732-736.

Li et al., "Folate-Mediated Targeting of Antisense Oligodeoxynucleotides to Ovarian Cancer Cells", Pharmaceutical Research, vol. 15, No. 10, 1998, pp. 1540-1545.

Citro et al., "Inhibition of leukemia cell proliferation by folic acid-polylysine-mediated introduction of c-myb antisense oligodeoxynucleotides into HL-60 cells", Br. J. Cancer (1994), 69, pp. 463-467.

Martindale, The Extra Pharmacopeia., J. Reynolds (ed.), p. 1160, The Pharmaceutical Press: London, GB (1988).

U.S. Appl. No. 12/743,191, filed May 14, 2010, Leamon et al.

Saha et al., "Toxic shock syndrome toxin-1-induced death is prevented by CTLA4Ig," J. Immunol., 1996, 157(9), 3869-3875.

Kuge et al., "Superantigen-induced human CD4+ helper/killer T cell phenomenon. Selective induction of Th1 helper/killer T cells and application to tumor immunotherapy," J. Immunol., 1995, 154(4), 1776-1785.

Lando et al., "T cell killing of human colon carcinomas by monoclonal-antibody-targeted superantigens," Cancer Immunol. Immunother., 1993, 36(4), 223-228.

Litton et al., "Antibody-targeted superantigen therapy induces tumor-infiltrating lymphocytes, excessive cytokine production, and apoptosis in human colon carcinoma," Eur. J. Immunol., 1996, 26(1), 1-9.

Galili et al., "One percent of human circulating B lymphocytes are capable of producing the natural anti-Gal antibody," Blood, 1993, 82(4), 2485-2493.

Galili et al., "Evolutionary relationship between the natural anti-Gal antibody and the Gal alpha 1—3Gal epitope in primates," PNAS, 1987, 84(5),1369-1373.

Bacha, P., et al., "Interleukin 2 receptor-targeted cytotoxicity. Interleukin 2 receptor-mediated action of a diphtheria toxin-related interleukin 2 fusion protein," J. Exp. Med., 1988; 167(2):612-622.

Batra, J., et al., "Anti-Tac(Fv)-PE40, a single chain antibody Pseudomonas fusion protein directed at interleukin 2 receptor bearing cells," J. Biol. Chem., 1990; 265(25): 15198-15202.

Benjamin, R., et al., "Induction of tolerance by monoclonal antibody therapy," Nature, 1986; 320(6061):449-451.

Borrebaeck, C., et al., "Does endogenous glycosylation prevent the use of mouse monoclonal antibodies as cancer therapeutics?" Immunol. Today, 1993; 14(10):477-479.

Buelow, R., et al., "Prolongation of skin allograft survival in mice following administration of allotrap," Transplantation, 1995; 59(4):455-460.

Dohlsten, M., et al., "Monoclonal antibody-targeted superantigens: a different class of anti-tumor agents," Proc. Natl. Acad. Sci. USA, 1991; 88(20):9287-9291.

Dohlsten, M., et al., "Targeting of human cytotoxic T lymphocytes to MHC class II-expressing calls by staphylococcal enterotoxins," Immunology, 1990; 71(1):96-100.

Galili, U., "Interaction of the natural anti-Gal antibody with α-galactosyl epitopes: a major obstacle for xenotransplantation in humans," Immunol. Today, 1993; 14(10):480-482.

Galili, U., at al., "A unique natural human IgG antibody with anti-α-galactosyl specificity," J. Exp. Med., 1984; 160(5):1519-1531.

Garrido, M., et al., "Targeting human T-lymphocytes with bispecific antibodies to react against human ovarian carcinoma cells growing in nu/nu mice," Cancer Res., 1990; 50(14):4227-4232.

Gravelle, M., et al., "The targeting of CD4+ T lymphocytes to a B cell lymphoma. A comparison of anti-CD3-anti-idiotype antibody conjugates and antigen-anti-idiotype antibody conjugates," J Immunol., 1989; 142(11):4079-4084.

Hall, W., et al., "In vitro efficacy of transferrin-toxin conjugates against glioblastoma multiforme," J. Neurosurg., 1992; 76(5):838-844.

Harris, W., et al., "Therapeutic antibodies-the coming of age," Trends Biotechnol., 1993; 11(2):42-44.

Junghans, R., et al., "Anti-Tac-H, a humanized antibody to the Interleukin 2 receptor with new features for immunotherapy in malignant and immune disorders," Cancer Res., 1990; 50(5):1495-1502.

Kotb, M., et al., "Accessory cell-independent stimulation of human T cells by streptococcal M protein superantigen," J. Immunol. 1990; 145(5):1332-1336.

Lando, P., et al., "Co-stimulation with B7 and targeted superantigen is required for MHC class II-independent T-cell proliferation but not cytotoxicity," Immunology, 1993; 80(2):236-241.

Leamon, C., et al., "Cytotoxicity of folate-Pseudomonas exotoxin conjugates toward tumor cells," J. Biol. Chem., 1993; 268(33):24847-24854.

Legaard, P., et al., "The superantigen Pseudomonas exotoxin A requires additional functions from accessory cells for T lymphocyte proliferation," Cell. Immunol., 1991; 135(2):372-382.

Liu, H., et al., "Conventional antigen and superantigen may be coupled to distinct and cooperative T-cell activation pathways," Proc. Natl. Acad. Sci. USA, 1991; 88(19):8705-8709.

Lorberboum-Galski, H., et al., "Cytotoxic activity of an Interleukin 2-Pseudomonas exotoxin chimeric protein produced in Escherichia coli," Proc. Natl. Acad. Sci USA, 1988; 85(6):1922-1926.

Ochi, A., et al., "A novel strategy for immunotherapy using antibody-coupled carriers to focus cytotoxic T helper cells," Eur. J. Immunol., 1987; 17(11): 1645-1648.

Ochi, A., et al., "In vivo tumor immunotherapy by a bacterial superantigen," J. Immunol., 1993; 151(6):3180-3186.

Osband, M., et al., "Problems in the investigational study and clinical use of cancer immunotherapy," *Immunol. Today*, 1990; 11(6):193-195.

Pullen, A., et al., "Identification of the region of T cell receptor β chain that interacts with the self-superantigen Mls-1 a," *Cell*, 1990; 61(7):1365-1374.

Renner, C., et al., "Tumor therapy by immune recruitment with bispecific antibodies," *Immunol. Rev.*, 1995; 145:179-209.

Sato, J., et al., "Enhancement of anti-tumor activity of recombinant interleukin-2 (rIL-2) by immunocomplexing with a monoclonal antibody against rIL-2," *Biotherapy*, 1993; 6(3):225-231.

Schroeder, T., et al., "Antimurine antibody formation following OKT3 therapy," *Transplantation*, 1990; 49(1):48-51.

Staerz, U., et al., "Hybrid antibodies can target sites for attack by T cells," *Nature*, 1985; 314(6012):628-31.

Staerz, U., et al., "Hybrid hybridoma producing a bispecific monoclonal antibody that can focus effector T-cell activity," *Proc. Nat. Acad. Sci. USA*, 1986; 83(5):1453-1457.

Van Ravenswaay, et al., "Analysis of production, purification, and cytolytic potential of bi-specific antibodies reactive with ovarian-carcinoma-associated antigens and the T-cell antigen CD3," *Int. J. Cancer*, 1993; 55:128-136.

Waldmann, T., "Monoclonal antibodies in diagnosis and therapy," *Science*, 1991; 252(5013):1657-1662.

Lu et al., "Folate receptor-targeted immunotherapy: induction of humoral and cellular immunity against hapten-decorated cancer cells," Int. J. Cancer, 2005; 116:710-719.

Lussow et al., "Targeting of activated T-cells with natural cytotoxic antibodies via an IL2-hapten conjugate prolongs graft survival," Transplantation Proceedings, 1996, 28(2), 571-572.

Alberts, B., Molecular Biology of the Cell, 3rd ed., pp. 1169-1170, Garland Publishing: New York, NY (1994).

Anon., Oxford Dictionary of Biochemistry and Molecular Biology, pp. 155, 216, A. Smith (ed.), Oxford University Press: Oxford, GB 91997.

Berkow, R., et al., The Merck Manual, p. 353, Merck & Co.: Rahway, NJ (1992).

Edgington, S., "How sweet it is: selectin-mediating drugs," Biotechnology, 1992; 10(4):383-389.

Green, C., "The ABO, Lewis and related blood group antigens; a review of structure and biosynthesis," FEMS Microbiol. Immunol., 1989; 1(6-7):321-330.

Kaplan, M., et al., "Flow rate dependence of in vitro removal of anti-A and anti-B antibodies by immunoadsorbents with synthetic oligosaccharides representing blood group substances," Int. J. Artif. Organs, 1989; 12(12):799-804.

Murphy, J., "Diphtheria-related peptide hormone gene fusions: A molecular genetic approach to chimeric toxin," in Immunotoxins, pp. 123-140, A. Frankel (ed.), Kluwer Academic Press: New York, NY (1988).

Roitt, I., et al., Roitt's Essential Immunology, pp. 48-49, Blackwell Publishing: Oxford, GB (1988).

Rosen. et al., Dictionary of Immunology, p. 140, Stockton Press: Hampshire, GB (1989).

Soulillou, J.P., "Biological reagents for immunosuppressants," Transplant Proc., 1995; 27(1):106-108.

Strom, T., et al., "Genetically engineered proteins for immunoregulation," Transplant. Proc., 1995; 27 (5 Supp. 1):18-20.

Tufveson, G., et al., "New immunosuppressants: testing and development in animal models and the clinic: with special reference to DSG," Immunol. Rev., 1993; 136:99-109.

Hoshino et al., "In vitro cytotoxicities and in vivo distribution of transferrin-platinum(II) complex," J. Pharm. Sci., 1995; 84(2):216-221.

Gobbo et al., "Synthesis and biological activity of the mono- and di-galactosyl-vespulakinin 1 analogues," Int. J. Peptide Protein Res., 1992; 40: 54-61.

Wood et al., "A Novel Method for the Incorporation of Glycoprotein-Derived Oligosaccharides into Neoglycopeptides," Bioconjugate Chem., 1992; 3:391-396.

Filira et al., "Synthesis of O-glycosylated tuftsins by utilizing threonine derivatives containing an unprotected monosaccharide moiety," Int. J. Peptide Protein Res., 1990; 36:86-96.

Galili et al., "Human Natural Anti-α-galactosyl IgG. II. The Specific Recognition of α(1→3)-linked Galactose Residues," J. Exp. Med., 1985; I62(2):573-582.

Nanzando's Medical Dictionary, pp. 1574, Hapten (Feb. 1, 1990).

Kazimierczuk et al., "Stereospecific synthesis by the sodium salt glycosylation method of halogeno benzimidazole 2'-deoxyribose analogues of the inhibitor of hnRNA synthesis, 5,6-dichloro-1-(beta-D-ribofuranosyl)benzimidazole (DRB)," Z Naturforsch C. Sep.-Oct. 1985;40(9-10):715-20.

Rademann et al., "Solid-phase synthesis of a glycosylated hexapeptide of human sialophorin, using the trichloroacetimidate method," Carbohydr Res. Apr. 19, 1995;269(2):217-25.

Wong Sy et al, "Synthetic glycosylation of peptides using unprotected saccharide beta-glycosylamines," Glycoconj J. Jun. 1993;10(3):227-34.

\* cited by examiner

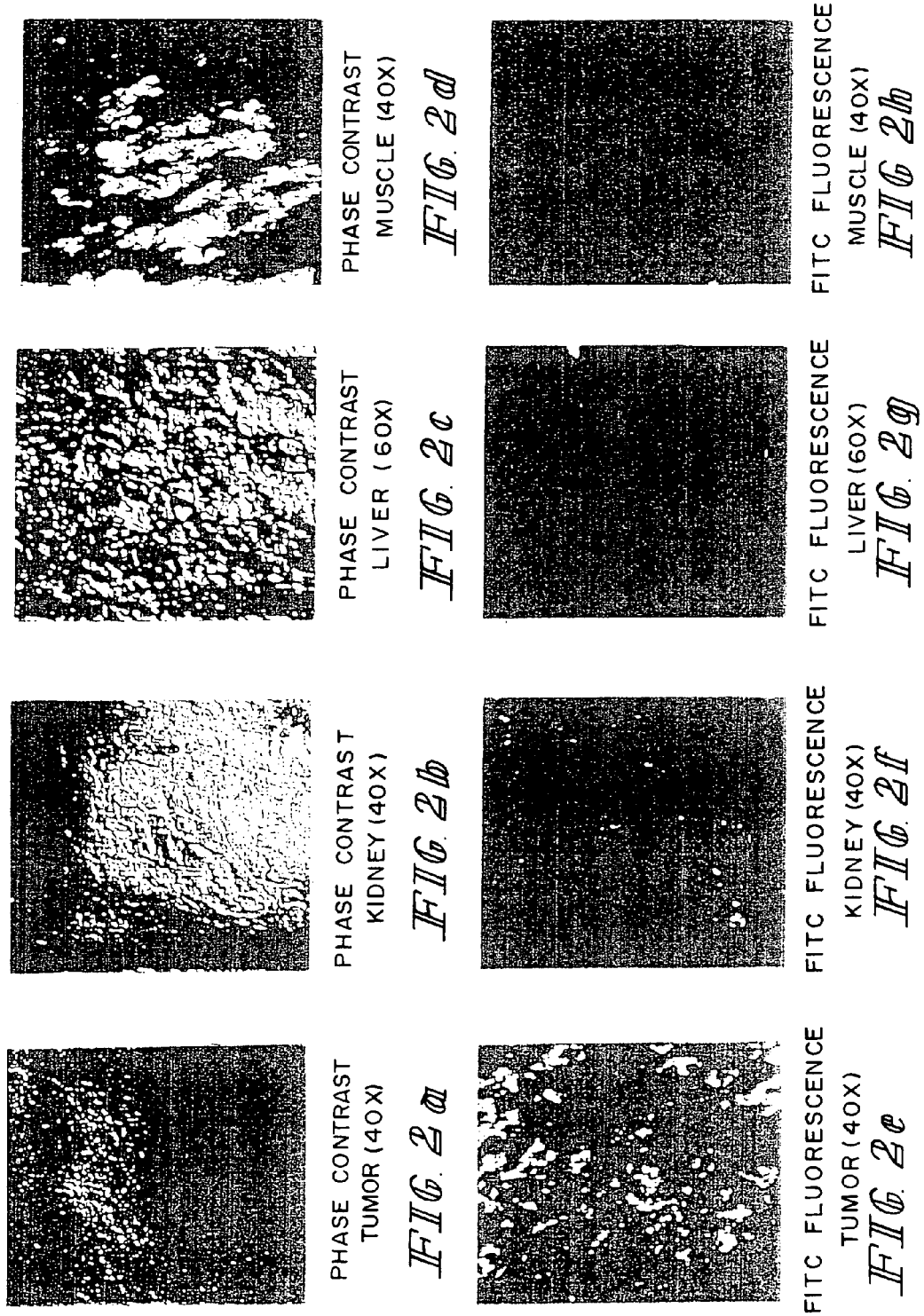

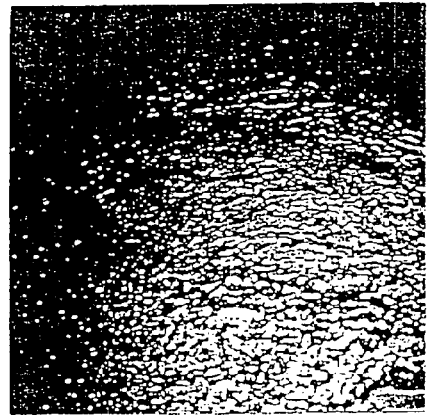
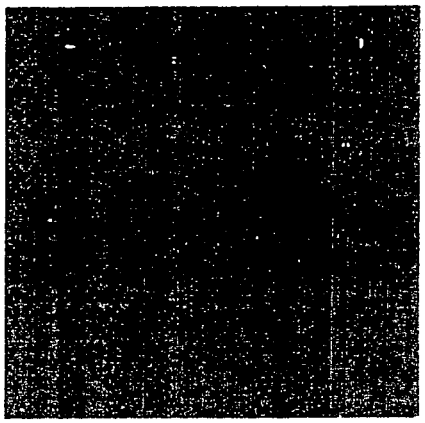
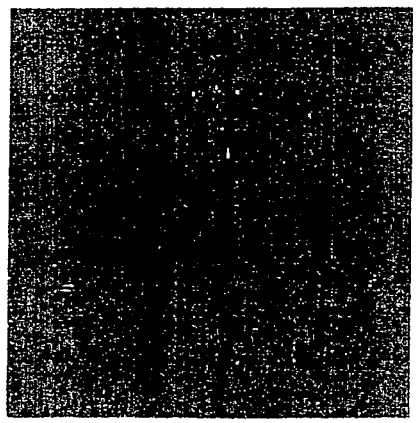
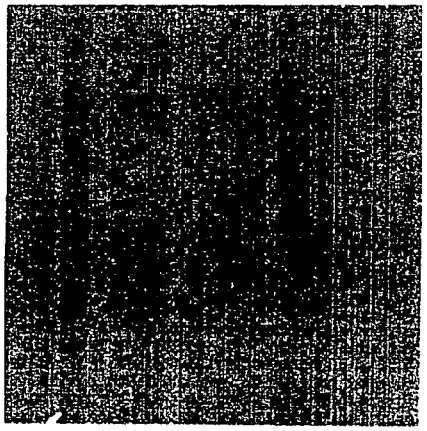
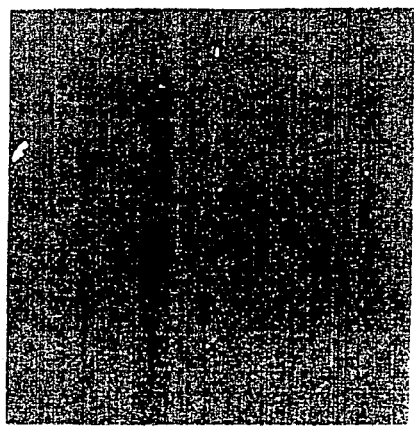

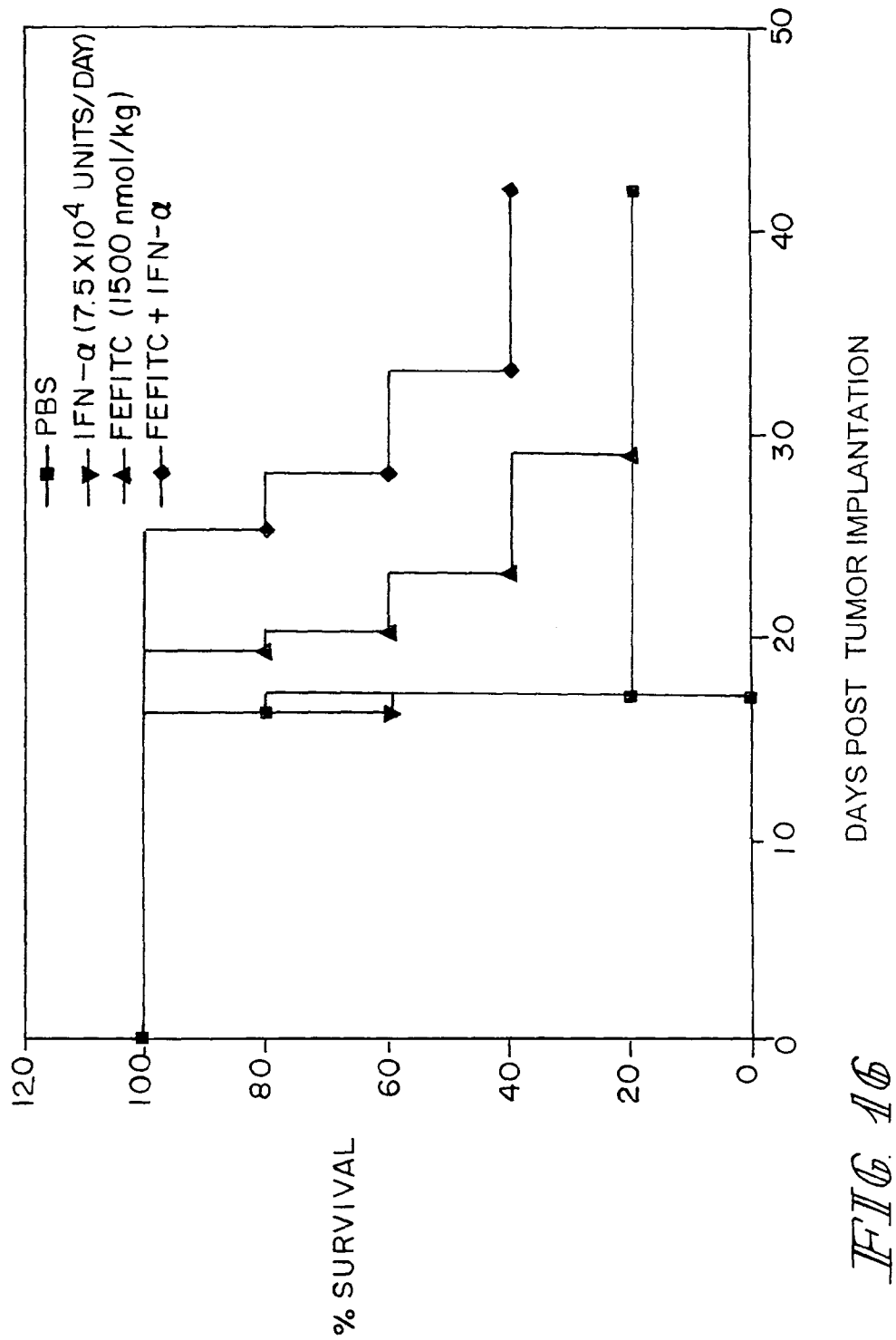

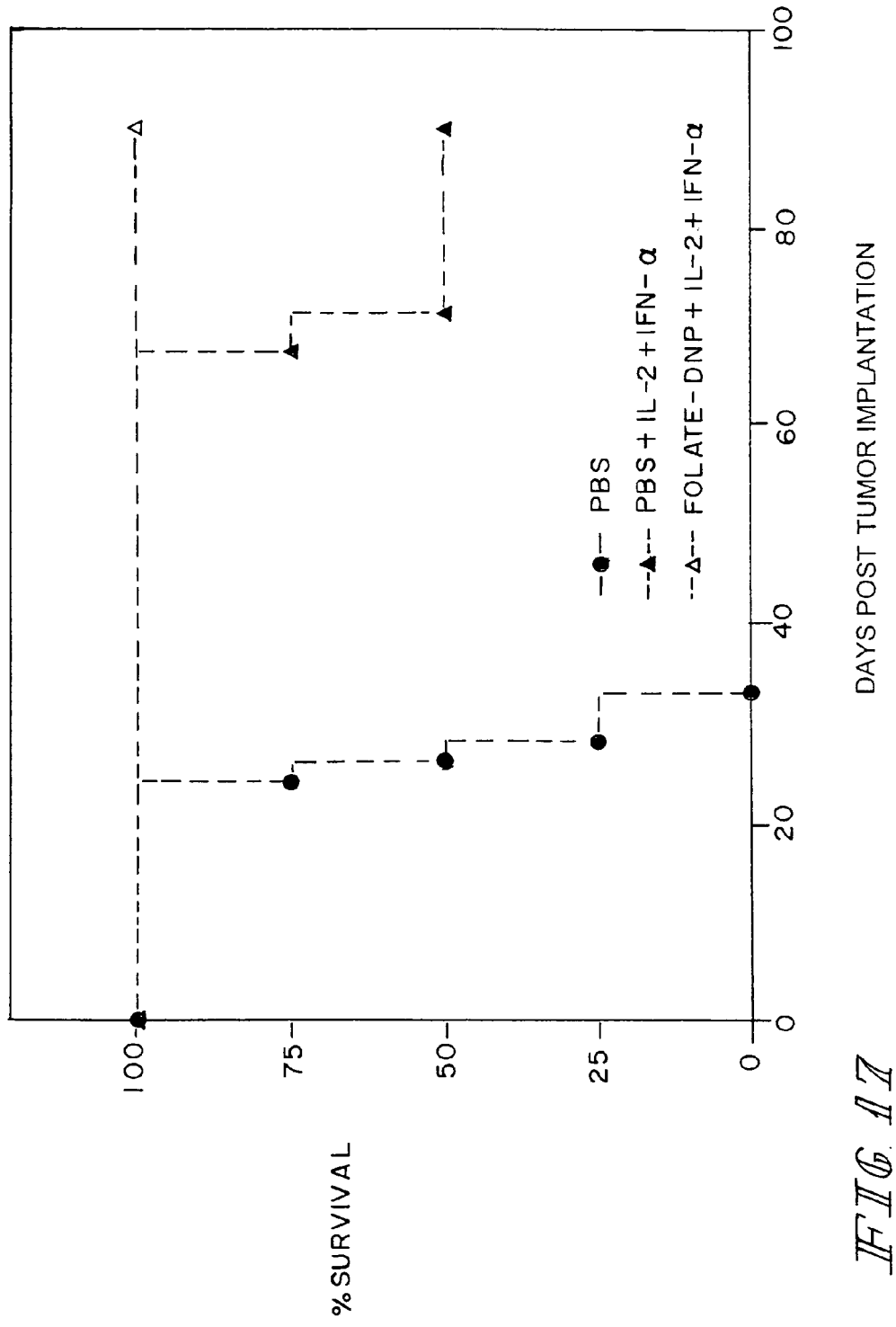

ence of pathogenic cell populations. More particularly, cell-targeted ligand-immunogen complexes are administered to a diseased host, preferably in combination with an immune system stimulant or other therapeutic factor, to enhance and/or redirect host immune responses to the pathogenic cells.

METHOD OF TREATMENT USING LIGAND-IMMUNOGEN CONJUGATES

CROSS REFERENCE TO RELATED APPLICATIONS

This application is a continuation application of U.S. patent application Ser. No. 09/822,379, filed Mar. 30, 2001 now U.S. Pat. No.7,033,594, which claims priority under 35 U.S.C. §119(e) to U.S. Provisional Application No. 60/193,944, filed Mar. 31, 2000, and to U.S. Provisional Application No. 60/255,846, filed Dec. 15, 2000, which are expressly incorporated by reference herein.

FIELD OF THE INVENTION

This invention relates to a method and pharmaceutical composition for use in treating disease states characterized by the existence of pathogenic cell populations. More particularly, cell-targeted ligand-immunogen complexes are administered to a diseased host, preferably in combination with an immune system stimulant or other therapeutic factor, to enhance and/or redirect host immune responses to the pathogenic cells.

BACKGROUND AND SUMMARY OF THE INVENTION

The mammalian immune system provides a means for the recognition and elimination of tumor cells, other pathogenic cells, and invading foreign pathogens. While the immune system normally provides a strong line of defense, there are still many instances where cancer cells, other pathogenic cells, or infectious agents evade a host immune response and proliferate or persist with concomitant host pathogenicity. Chemotherapeutic agents and radiation therapies have been developed to eliminate replicating neoplasms. However, most, if not all, of the currently available chemotherapeutic agents and radiation therapy regimens have adverse side effects because they work not only to destroy cancer cells, but they also affect normal host cells, such as cells of the hematopoietic system. Furthermore, chemotherapeutic agents have limited efficacy in instances where host drug resistance is developed.

Foreign pathogens can also proliferate in a host by evading a competent immune response or where the host immune system has been compromised by drug therapies or by other health problems. Although many therapeutic compounds have been developed, many pathogens are or have become resistant to such therapeutics. The capacity of cancer cells and infectious organisms to develop resistance to therapeutic agents, and the adverse side effects of the currently available anticancer drugs, highlight the need for the development of new therapies specific for pathogenic cell populations with reduced host toxicity.

Researchers have developed therapeutic protocols for destroying cancer cells by targeting cytotoxic compounds specifically to such cells. These protocols utilize toxins conjugated to ligands that bind to receptors unique to or overexpressed by cancer cells in an attempt to minimize delivery of the toxin to normal cells. Using this approach certain immunotoxins have been developed consisting of antibodies directed to specific receptors on pathogenic cells, the antibodies being linked to toxins such as ricin, Pseudomonas exotoxin, Diptheria toxin, and tumor necrosis factor. These immunotoxins target tumor cells bearing the specific receptors recognized by the antibody (Olsnes, S., *Immunol. Today,* 10, pp. 291-295, 1989; Melby, E. L., *Cancer Res.,* 53(8), pp. 1755-1760, 1993; Better, M. D., PCT Publication Number WO 91/07418, published May 30, 1991).

Another approach for selectively targeting populations of cancer cells or foreign pathogens in a host is to enhance host immune response against the pathogenic cells, thereby avoiding the need for administration of compounds that may also exhibit independent host toxicity. One reported strategy for immunotherapy is to bind antibodies, for example, genetically engineered multimeric antibodies, to the tumor cell surface to display the constant region of the antibodies on the cell surface and thereby induce tumor cell killing by various immune-system mediated processes. (DeVita, V. T., *Biologic Therapy of Cancer,* 2d ed. Philadelphia, Lippincott, 1995; Soulillou, J. P., U.S. Pat. No. 5,672,486). However, this approach has been complicated by the difficulties in defining tumor-specific antigens. Another approach to relying on host immune competency is the targeting of an anti-T cell receptor antibody or anti-Fc receptor antibody to tumor cell surfaces to promote direct binding of immune cells to tumors (Kranz, D. M., U.S. Pat. No. 5,547,668). A vaccine-based approach has also been described which relies on a vaccine comprising antigens fused to cytokines, with the cytokine modifying the immunogenicity of the vaccine antigen, and, thus, stimulating the immune response to the pathogenic agent (Pillai, S., PCT Publication Number WO 91/11146, published Feb. 7, 1991). That method relies on indirect modulation of the immune response reported. Another approach for killing unwanted cell populations utilizes IL-2 or Fab fragments of anti-thymocyte globulin linked to antigens to eliminate unwanted T cells; however, based on reported experimental data, the method appears to eliminate only 50% of the targeted cell population, and results in nonspecific cell killing in vivo (i.e., 50% of peripheral blood lymphocytes that are not T cells are also killed (Pouletty, P., PCT publication number WO 97/37690, published Oct. 16, 1997)). Thus, there remains a significant need for therapies directed to treatment of disease states characterized by the existence of pathogenic cell populations in an affected host.

The present invention is directed to a method of eliminating pathogenic cell populations in a host by increasing host immune system recognition of and response to such cell populations. Effectively, the antigenicity of the cellular pathogens is increased to enhance the endogenous immune response-mediated elimination of the population of pathogenic cells. The method avoids or minimizes the use of cytotoxic or antimicrobial therapeutic agents. The method comprises administration of a ligand-immunogen conjugate wherein the ligand is capable of specific binding to a population of pathogenic cells in vivo that uniquely expresses, preferentially expresses, or overexpresses a ligand binding moiety, and the ligand conjugated immunogen is capable of eliciting antibody production or, more preferably, capable of being recognized by endogenous or co-administered exogenous antibodies in the host animal. The immune system mediated elimination of the pathogenic cells is directed by the binding of the immunogen conjugated ligand to a receptor, a transporter, or other surface-presented protein uniquely expressed, overexpressed, or preferentially expressed by the pathogenic cell. A surface-presented protein uniquely expressed, overexpressed, or preferentially expressed by the pathogenic cell is a receptor not present or present at lower amounts on non-pathogenic cells providing a means for selective elimination of the pathogenic cells. At least one additional therapeutic factor, for example, an immune system stimulant, a cell killing agent, a tumor penetration enhancer, a chemotherapeutic agent, a cytotoxic immune cell, or an antimicrobial agent may be co-administered to the host animal to enhance therapeutic efficiency.

In one embodiment, the present method includes the steps of administering ligands capable of high affinity specific binding in vivo to cell surface proteins uniquely expressed, preferentially expressed, or overexpressed on the targeted pathogenic cell population, said ligands being conjugated to immunogens against which an innate or an acquired immunity already exists or can be elicited in the host animal, and optionally co-administration of at least one therapeutic factor that is an endogenous immune response activator or a cytotoxic compound. In one preferred embodiment the method involves administering a ligand-immunogen conjugate composition to the host animal wherein the ligand is folic acid or another folate receptor binding ligand. The ligand is conjugated, for example, by covalent binding, to an immunogen capable of eliciting an antibody response in the host animal or, more preferably, an immunogen capable of binding to preexisting endogenous antibodies (consequent to an innate or acquired immunity) or co-administered antibodies (i.e., via passive immunization) in the host animal. At least one additional therapeutic factor, not capable of specific binding to the ligand-immunogen complex, but capable of stimulating or enhancing an endogenous immune response, a cell killing agent, a tumor penetration enhancer, such as an inflammatory or proinflammatory agent, a chemotherapeutic agent, a cytotoxic immune cell, or an antimicrobial agent can be administered to the host animal in conjunction with administration of the ligand-immunogen conjugates.

In accordance with another embodiment of the invention there is provided a method of enhancing an endogenous immune response-mediated specific elimination of a population of pathogenic cells in a host animal harboring said population wherein the members of said cell population have an accessible binding site for a ligand. The method comprises the step of administering to said host a ligand-immunogen conjugate composition comprising a complex of the ligand and an immunogen wherein said immunogen is known to be recognized by an endogenous or an exogenous antibody in the host or is known to be recognized directly by an immune cell in the host, and at least one additional composition comprising a therapeutic factor, said factor being selected from the group consisting of a cell killing agent, a tumor penetration enhancer, a chemotherapeutic agent, an antimicrobial agent, a cytotoxic immune cell, and a compound capable of stimulating an endogenous immune response wherein the compound does not bind to the ligand-immunogen conjugate.

In accordance with an alternative embodiment of the invention, there is provided a method of enhancing an endogenous immune response-mediated specific elimination of a population of pathogenic cells in a host animal harboring said population wherein said population expresses a binding site for a ligand. The method comprises the steps of administering to the host a composition comprising a complex of said ligand and an immunogen, administering to the host antibodies directed against the immunogen, and administering to said host at least one additional therapeutic factor, said factor being selected from the group consisting of a cell killing agent, a tumor penetration enhancer, a chemotherapeutic agent, an antimicrobial agent, a cytotoxic immune cell, and a stimulant of an endogenous immune response that does not bind to the ligand-immunogen complex.

In one preferred embodiment of the invention, there is provided a method of enhancing an endogenous immune response-mediated specific elimination of a population of pathogenic cells in a host animal harboring said population wherein said population preferentially expresses, uniquely expresses, or overexpresses a folic acid receptor. The method comprises the step of administering to said host a composition comprising a covalently linked conjugate of an immunogen wherein the immunogen is known to be recognized by an endogenous or exogenous antibody in the host or is known to be recognized directly by an immune cell in the host, and a ligand comprising folic acid or a folic acid analogue having a glutamyl group wherein the covalent linkage to the immunogen is only through the γ-carboxy group of the glutamyl group. In another embodiment at least one additional composition is administered to the host comprising a therapeutic factor, said factor being selected from the group consisting of a cell killing agent, a tumor penetration enhancer, a chemotherapeutic agent, an antimicrobial agent, a cytotoxic immune cell, and a compound capable of stimulating an endogenous immune response wherein the compound does not bind to the ligand-immunogen conjugate.

In yet another embodiment of the invention, there is provided a method of enhancing an endogenous immune response-mediated specific elimination of a population of pathogenic cells in a host animal harboring said population wherein said population preferentially expresses, uniquely expresses, or overexpresses a folic acid receptor. The method comprises the step of administering to said host a composition comprising a covalently linked conjugate of an immunogen wherein the immunogen is known to be recognized by an endogenous or exogenous antibody in the host or is known to be recognized directly by an immune cell in the host, and a ligand comprising folic acid or a folic acid analogue having a glutamyl group wherein the covalent linkage to the immunogen is only through the α-carboxy group of the glutamyl group. In another embodiment at least one additional composition is administered to the host comprising a therapeutic factor, said factor being selected from the group consisting of a cell killing agent, a tumor penetration enhancer, a chemotherapeutic agent, an antimicrobial agent, a cytotoxic immune cell, and a compound capable of stimulating an endogenous immune response wherein the compound does not bind to the ligand-immunogen conjugate.

In still one other embodiment of this invention, the targeted pathogenic cell population is a cancer cell population. In another embodiment the targeted cell population are virus-infected endogenous cells. In another embodiment the targeted cell population is a population of exogenous organisms such as bacteria, mycoplasma yeast or fungi. The ligand-immunogen conjugate binds to the surface of the tumor cells or pathogenic organisms and "labels" the cell members of the targeted cell population with the immunogen, thereby triggering an immune mediated response directed at the labeled cell population. Antibodies administered to the host in a passive immunization or antibodies existing in the host system from a preexisting innate or acquired immunity bind to the immunogen and trigger endogenous immune responses. Antibody binding to the cell-bound ligand-immunogen conjugate results in complement-mediated cytotoxicity, antibody-dependent cell-mediated cytotoxicity, antibody opsonization and phagocytosis, antibody-induced receptor clustering signaling cell death or quiescence or any other humoral or cellular immune response stimulated by antibody binding to cell-bound ligand-immunogen conjugates. In cases where an antigen can be directly recognized by immune cells without prior antibody opsonization, direct killing of pathogenic cells can occur.

Elimination of the foreign pathogens or infected or neoplastic endogenous cells can be further enhanced by administering a therapeutic factor capable of stimulating an endogenous immune response, a cell killing agent, a tumor penetration enhancer, a chemotherapeutic agent, a cytotoxic immune cell, or an antimicrobial agent. In one embodiment, the cytotoxic immune cell is a cytotoxic immune cell population that is isolated, expanded ex vivo, and is then injected into a host animal. In another embodiment of the invention an immune stimulant is used and the immune stimulant may be an interleukin such as IL-2, IL-12, or IL-15 or an IFN such as IFN-α, IFN-β, or IFN-γ, or GM-CSF. In another embodiment the immune stimulant may be a cytokine composition comprising combinations of cytokines, such as IL-2, IL-12 or IL-15 in combination with IFN-α, IFN-β, or IFN-γ, or GM-CSF, or any effective combination thereof, or any other effective combination of cytokines.

In still one other embodiment of the invention, there is provided a pharmaceutical composition comprising therapeutically effective amounts of a ligand-immunogen conjugate capable of specific binding to a population of pathogenic cells in a host animal to promote specific elimination of said cells by an acquired or innate immune response, co-administered antibodies, or directly by an immune cell in the host, a therapeutic factor selected from the group consisting of a cell killing agent, a tumor penetration enhancer, a chemotherapeutic agent, an antimicrobial agent, a cytotoxic immune cell, and a compound capable of stimulating an endogenous immune response wherein the compound does not bind to the ligand-immunogen conjugate, and a pharmaceutically acceptable carrier therefor. In one embodiment the pharmaceutical composition is in a parenteral prolonged release dosage form. In another embodiment the therapeutic factor is an immune stimulant comprising a compound selected from the group consisting of interleukins such as IL-2, IL-12, IL-15, IFNs such as IFN-α, IFN-β, or IFN-γ, and GM-CSF, or combinations thereof.

BRIEF DESCRIPTION OF THE DRAWINGS

FIG. 2 shows phase contrast and FITC fluorescence micrographs of slices of various tissues.

FIG. 3 shows untreated tumor tissues and folate-FITC treated tumor tissues examined for FITC and PE fluorescence and examined by phase contrast microscopy as described in EXAMPLE 3.

FIG. 16 shows the synergistic effect of folate conjugates and cytokines on long-term survival of mice.

FIG. 17 shows the effect of folate-targeted immunotherapy on long-term survival of mice.

DETAILED DESCRIPTION OF THE INVENTION

Figure 1:
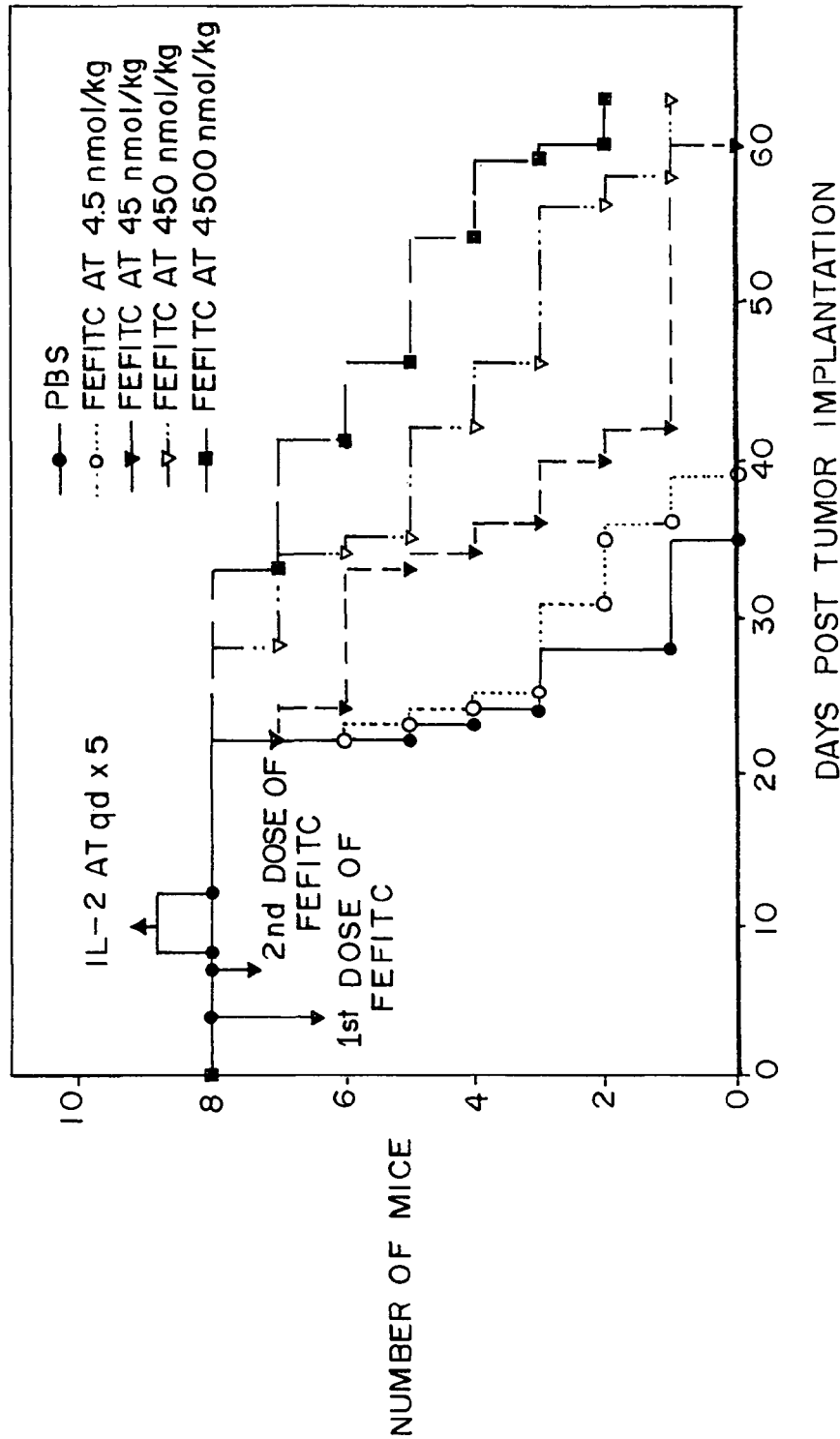
FIG. 1 shows the effect of folate-targeted immunotherapy on the survival of mice with lung tumor implants.

Methods are provided for the therapeutic treatment of a host with cancer or a host infected with pathogenic organisms. The methods result in enhancement of the immune response-mediated elimination of pathogenic cell populations by rendering/labeling the pathogenic cells antigenic resulting in their recognition and elimination by the host immune system. The method employs a ligand-immunogen conjugate capable of high affinity binding to cancer cells or other pathogenic agents. The high affinity binding can be inherent to the ligand and it may be modified (enhanced) by the use of a chemically modified ligand or from the particular chemical linkage between the ligand and the immunogen that is present in the conjugate. The method may also utilize combination therapy by employing the ligand-immunogen conjugate and an additional therapeutic factor capable of stimulating an endogenous immune response, a cell killing agent, a chemotherapeutic agent, a tumor penetration enhancer, a cytotoxic immune cell, or an antimicrobial agent to enhance immune response-mediated elimination of the pathogenic cell populations.

The method of the present invention is utilized to enhance an endogenous immune response-mediated elimination of a population of pathogenic cells in a host animal harboring the population of pathogenic cells. The invention is applicable to populations of pathogenic cells that cause a variety of pathologies such as cancer and infectious diseases. Thus, the population of pathogenic cells may be a cancer cell population that is tumorigenic, including benign tumors and malignant tumors, or it can be non-tumorigenic. The cancer cell population may arise spontaneously or by such processes as mutations present in the germline of the host animal or somatic mutations, or it may be chemically-, virally-, or radiation-induced. The invention can be utilized to treat such cancers as carcinomas, sarcomas, lymphomas, Hodgekin's disease, melanomas, mesotheliomas, Burkitt's lymphoma, nasopharyngeal carcinomas, leukemias, and myelomas. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers.

The population of pathogenic cells may also be an exogenous pathogen or a cell population harboring an exogenous pathogen, e.g., a virus. The present invention is applicable to such exogenous pathogens as bacteria, fungi, viruses, mycoplasma, and parasites. Infectious agents that may be treated with the present invention are any art-recognized infectious organisms that cause pathogenesis in an animal, including such organisms as bacteria that are gram-negative or gram-positive cocci or bacilli, DNA and RNA viruses, including, but not limited to, DNA viruses such as papilloma viruses, parvoviruses, adenoviruses, herpesviruses and vaccinia viruses, and RNA viruses, such as arenaviruses, coronaviruses, rhinoviruses, respiratory syncytial viruses, influenza viruses, picornaviruses, paramyxoviruses, reoviruses, retroviruses, and rhabdoviruses. Of particular interest are bacteria that are resistant to antibiotics such as antibiotic-resistant *Streptococcus* species and *Staphlococcus* species, or bacteria that are susceptible to antibiotics, but cause recurrent infections treated with antibiotics so that resistant organisms eventually develop. Such organisms can be treated with the ligand-immunogen conjugates of the present invention in combination with lower doses of antibiotics than would normally be administered to a patient to avoid the development of these antibiotic-resistant bacterial strains. The present invention is also applicable to any fungi, mycoplasma species, parasites, or other infectious organisms that cause disease in animals. Examples of fungi that may be treated with the method of the present invention include fungi that grow as molds or are yeastlike, including, for example, fungi that cause diseases such as ringworm, histoplasmosis, blastomycosis, aspergillosis, cryptococcosis, sporotrichosis, coccidioidomycosis, paracoccidio-idomycosis, and candidiasis. The present invention may be utilized to treat parasitic infections including, but not limited to, infections caused by somatic tapeworms, blood flukes, tissue roundworms, ameba, and *Plasmodium, Trypanosoma, Leishmania*, and *Toxoplasma* species. Parasites of particular interest are those that express folate receptors and bind folate; however, the literature is replete with reference to ligands exhibiting high affinity for infectious organisms. For example, penicillins and cephalosporins known for their antibiotic activity and specific binding to bacterial cell wall precursors can similarly be used as ligands for preparing ligand-immunogen conjugates for use in accordance with this invention. The ligand-immunogen conjugates of the invention may also be directed to a cell population harboring endogenous pathogens wherein pathogen-specific antigens are preferentially expressed on the surface of cells harboring the pathogens, and act as receptors for the ligand with the ligand specifically binding to the antigen.

The method of the present invention can be used for both human clinical medicine and veterinary applications. Thus, the host animals harboring the population of pathogenic organisms and treated with ligand-immunogen conjugates may be humans or, in the case of veterinary applications, may be a laboratory, agricultural, domestic, or wild animals. The present invention can be applied to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The ligand-immunogen conjugate is preferably administered to the host animal parenterally, e.g., intradermally, subcutaneously, intramuscularly, intraperitoneally, or intravenously. Alternatively, the conjugate may be administered to the host animal by other medically useful processes, and any effective dose and suitable therapeutic dosage form, including prolonged release dosage forms, can be used. The method of the present invention may be used in combination with surgical removal of a tumor, radiation therapy, chemotherapy, or biological therapies such as other immunotherapies including, but not limited to, monoclonal antibody therapy, treatment with immunomodulatory agents, adoptive transfer of immune effector cells, treatment with hematopoietic growth factors, cytokines and vaccination.

In accordance with the present invention, the ligand-immunogen conjugates may be selected from a wide variety of ligands and immunogens. The ligands must be capable of specifically eliminating a population of pathogenic cells in the host animal due to preferential expression of a receptor for the ligand, accessible for ligand binding, on the pathogenic cells. Acceptable ligands include folic acid, analogs of folic acid and other folate receptor-binding molecules, other vitamins, peptide ligands identified from library screens, tumor-specific peptides, tumor-specific aptamers, tumor-specific carbohydrates, tumor-specific monoclonal or polyclonal antibodies, Fab or scFv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selectins, steroid hormones, Arg-Gly-Asp containing peptides, retinoids, various Galectins, δ-opioid receptor ligands, cholecystokinin A receptor ligands, ligands specific for angiotensin AT1 or AT2 receptors, peroxisome proliferator-activated receptor γ ligands, β-lactam antibiotics, small organic molecules including antimicrobial drugs, and other molecules that bind specifically to a receptor preferentially expressed on the surface of tumor cells or on an infectious organism, or fragments of any of these molecules. Of interest in the case of ligands that bind to infectious organisms, are any molecules, such as antibiotics or other drugs, that are known in the art to preferentially bind to the microorganism. The invention also applies to ligands which are molecules, such as antimicrobial drugs, designed to fit into the binding pocket of a particular receptor, based on the crystal structure of the receptor, or other cell surface protein, and wherein such receptors are preferentially expressed on the surface of tumors, bacteria, viruses, mycoplasma, fungi, parasites, or other pathogens. It is also contemplated, in a preferred embodiment of the invention, that ligands binding to any tumor antigens or other molecules preferentially expressed on the surface of tumor cells may be utilized.

The binding site for the ligand may include receptors for any molecule capable of specifically binding to a receptor wherein the receptor or other protein is preferentially expressed on the population of pathogenic cells, including, for example, receptors for growth factors, vitamins, peptides, including opioid peptides, hormones, antibodies, carbohydrates, and small organic molecules. The binding site may also be a binding site for any molecule, such as an antibiotic or other drug, where the site is known in the art to preferentially exist on microorganisms. For example, the subject binding sites may be binding sites in the bacterial cell wall for a β-lactam antibiotic such as penicillin, or binding sites for an antiviral agent uniquely present on the surface of a virus. The invention also applies to binding sites for ligands, such as antimicrobial drugs, designed to fit into the binding site of the receptor, based on the crystal structure of the receptor, and wherein the receptor is preferentially expressed on the surface of the pathogenic cells or organisms. It is also contemplated that tumor-specific antigens may function as binding sites for ligands in the method of the present invention. An example of a tumor-specific antigen that could function as a binding site for ligand-immunogen conjugates is an extracellular epitope of a member of the Ephrin family of proteins, such as EphA2. EphA2 expression is restricted to cell-cell junctions in normal cells, but EphA2 is distributed over the entire cell surface in metastatic tumor cells. Thus, EphA2 on metastatic cells would be accessible for binding to, for example, an Fab fragment of an antibody conjugated to an immunogen, whereas the protein would not be accessible for binding to the Fab fragment on normal cells, resulting in a ligand-immunogen conjugate specific for metastatic cancer cells. The invention further contemplates the use of combinations of ligand-immunogen conjugates to maximize targeting of the pathogenic cells for elimination by an acquired or innate immune response or by co-administered antibodies.

Acceptable immunogens for use in the present invention are immunogens that are capable of eliciting antibody production in a host animal or that have previously elicited antibody production in a host animal resulting in a preexisting immunity or that constitute part of the innate immune system. Alternatively, antibodies directed against the immunogen may be administered to the host animal to establish a passive immunity. Suitable immunogens for use in the invention include antigens or antigenic peptides against which a preexisting immunity has developed via normally scheduled vaccinations or prior natural exposure to such agents as poliovirus, tetanus, typhus, rubella, measles, mumps, pertussis, tuberculosis, and influenza antigens, and α-galactosyl groups. In such cases, the ligand-immunogen conjugates will be used to redirect a previously acquired humoral or cellular immunity to a population of pathogenic cells in the host animal for elimination of the foreign cells or pathogenic organisms. Other suitable immunogens include antigens or antigenic peptides to which the host animal has developed a novel immunity through immunization against an unnatural antigen or hapten (e.g., fluorescein isothiocyanate or dinitrophenyl) and antigens against which an innate immunity exists (e.g., super antigens and muramyl dipeptide).

The ligands and immunogens of the invention may be conjugated by utilizing any art-recognized method of forming a complex. This can include covalent, ionic, or hydrogen bonding of the ligand to the immunogen, either directly or indirectly via a linking group such as a divalent linker. The conjugate is typically formed by covalent bonding of the ligand to the immunogen through the formation of amide, ester or imino bonds between acid, aldehyde, hydroxy, amino, or hydrazo groups on the respective components of the complex. In a preferred embodiment of the invention, the ligand is folic acid, an analog of folic acid, or any other folate-receptor binding molecule, and the folate ligand is conjugated to the immunogen by a procedure that utilizes trifluoroacetic anhydride to prepare γ-esters of folic acid via a pteroyl azide intermediate. This preferred procedure results in the synthesis of a folate ligand, conjugated to the immunogen only through the γ-carboxy group of the glutamic acid groups of folate wherein the γ-conjugate binds to the folate receptor with high affinity, avoiding the formation of mixtures of an α-conjugate and the γ-conjugate. Alternatively, pure α-conjugates can be prepared from intermediates wherein the γ-carboxy group is selectively blocked, the α-conjugate is formed and the γ-carboxy group is subsequently deblocked using art-recognized organic synthesis protocols and procedures. Notably other vitamins can be employed as ligands for preparing the conjugates in accordance with this invention. For example, ligand-immunogen conjugates can be formed with biotin and riboflavin as well as folate. (See U.S. Pat. Nos. 5,108,921, 5,416,016, and 5,635,382 incorporated herein by reference.)

The ligand-immunogen conjugates of the invention enhance an endogenous immune response-mediated elimination of a population of pathogenic cells. The endogenous immune response may include a humoral response, a cell-mediated immune response, and any other immune response endogenous to the host animal, including complement-mediated cell lysis, antibody-dependent cell-mediated cytoxicity (ADCC), antibody opsonization leading to phagocytosis, clustering of receptors upon antibody binding resulting in signaling of apoptosis, antiproliferation, or differentiation, and direct immune cell recognition of the delivered antigen/hapten. It is also contemplated that the endogenous immune response will employ the secretion of cytokines that regulate such processes as the multiplication and migration of immune cells. The endogenous immune response may include the participation of such immune cell types as B cells, T cells, including helper and cytotoxic T cells, macrophages, natural killer cells, neutrophils, LAK cells and the like.

The humoral response may be a response induced by such processes as normally scheduled vaccination, or active immunization with a natural antigen or an unnatural antigen or hapten (e.g., fluorescein isothiocyanate), with the unnatural antigen inducing a novel immunity. Active immunization involves multiple injections of the unnatural antigen or hapten scheduled outside of a normal vaccination regimen to induce the novel immunity. The humoral response may also result from an innate immunity where the host animal has a natural preexisting immunity, such as an immunity to α-galactosyl groups. Alternatively, a passive immunity may be established by administering antibodies to the host animal such as natural antibodies collected from serum or monoclonal antibodies that may or may not be genetically engineered antibodies, including humanized antibodies. The utilization of a particular amount of an antibody reagent to develop a passive immunity, and the use of a ligand-immunogen conjugate wherein the passively administered antibodies are directed to the immunogen, would provide the advantage of a standard set of reagents to be used in cases where a patient's preexisting antibody titer to other potential antigens is not therapeutically useful. The passively administered antibodies may be "co-administered" with the ligand-immunogen conjugate and co-administration is defined as administration of antibodies at a time prior to, at the same time as, or at a time following administration of the ligand-immunogen conjugate.

It is contemplated that the preexisting antibodies, induced antibodies, or passively administered antibodies will be redirected to the tumor cells or infectious organisms by preferential binding of the ligand-immunogen conjugates to these invading cells or organisms and that the pathogenic cells will be killed by complement-mediated lysis, ADCC, antibody-dependent phagocytosis, or antibody clustering of receptors. The cytotoxic process may also involve other types of immune responses, such as cell-mediated immunity, as well as secondary responses that arise when the attracted antigen-presenting cells phagocytose the unwanted cells and present natural tumor antigens or antigens of foreign pathogens to the immune system for elimination of the cells or organisms bearing the antigens.

At least one additional composition comprising a therapeutic factor may be administered to the host in combination or as an adjuvant to the above-detailed methodology, to enhance the endogenous immune response-mediated elimination of the population of pathogenic cells, or more than one additional therapeutic factor may be administered. The therapeutic factor may be selected from a compound capable of stimulating an endogenous immune response, a chemotherapeutic agent, an antimicrobial agent, or other therapeutic factor capable of complementing the efficacy of the administered ligand-immunogen complex. The method of the invention can be performed by administering to the host, in addition to the above-described conjugates, compounds or compositions capable of stimulating an endogenous immune response including, but not limited to, cytokines or immune cell growth factors such as interleukins 1-18, stem cell factor, basic FGF, EGF, G-CSF, GM-CSF, FLK-2 ligand, HILDA, MIP-1α, TGF α, TGF β, M-CSF, IFN α, IFN β, IFN γ, soluble CD23, LIF, and combinations thereof.

Therapeutically effective combinations of these cytokines may also be used. In a preferred embodiment, for example, therapeutically effective amounts of IL-2, for example, in amounts ranging from about 5000 IU/dose/day to about 500,000 IU/dose/day in a multiple dose daily regimen, and IFN-α, for example, in amounts ranging from about 7500 IU/dose/day to about 150,000 IU/dose/day in a multiple dose daily regimen, are used along with folate-linked fluorescein isothiocynate to eliminate pathogenic cells in a host animal harboring such a population of cells. In another preferred embodiment IL-12 and IFN-α are used in therapeutically effective amounts, and in yet another preferred embodiment IL-15 and IFN-α are used in therapeutically effective amounts. In an alternate preferred embodiment IL-2, IFN-α or IFN-γ, and GM-CSF are used in combination. Preferably, the therapeutic factor(s) used, such as IL-2, IL-12, IL-15, IFN-α, IFN-γ, and GM-CSF, including combinations thereof, activate(s) natural killer cells and/or T cells. Alternatively, the therapeutic factor or combinations thereof, including an interleukin in combination with an interferon and GM-CSF, may activate other immune effector cells such as macrophages, B cells, neutrophils, LAK cells or the like. The invention also contemplates the use of any other effective combination of cytokines including combinations of other interleukins and interferons and colony stimulating factors.

Chemotherapeutic agents, which are cytotoxic themselves and can work to enhance tumor permeability, suitable for use in the method of the invention include adrenocorticoids, alkylating agents, antiandrogens, antiestrogens, androgens, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, cyclophosphamide, plant alkaloids, prednisone, hydroxyurea, teniposide, antibiotics such as mitomycin C and bleomycin, nitrogen mustards, nitrosureas, vincristine, vinblastine, inflammatory and proinflammatory agents, and any other art-recognized chemotherapeutic agent. Other therapeutic agents that can be administered adjuvant to the administration of the present conjugates, include penicillins, cephalosporins, vancomycin, erythromycin, clindamycin, rifampin, chloramphenicol, aminoglycosides, gentamicin, amphotericin B, acyclovir, trifluridine, ganciclovir, zidovudine, amantadine, ribavirin, and any other art-recognized antimicrobial compound.

The elimination of the population of pathogenic cells will comprise a reduction or elimination of tumor mass or of pathogenic organisms resulting in a therapeutic response. In the case of a tumor, the elimination may be an elimination of cells of the primary tumor or of cells that have metastasized or are in the process of dissociating from the primary tumor. A prophylactic treatment to prevent return of a tumor after its removal by any therapeutic approach including surgical removal of the tumor, radiation therapy, chemotherapy, or biological therapy is also contemplated in accordance with this invention. The prophylactic treatment may be an initial treatment with the ligand-immunogen conjugate, such as treatment in a multiple dose daily regimen, and/or may be an additional treatment or series of treatments after an interval of days or months following the initial treatments(s).

The invention is also directed to pharmaceutical compositions comprising an amount of a ligand-immunogen conjugate effective to "label" a population of pathogenic cells in a host animal for specific elimination by an endogenous immune response or by co-administered antibodies. The composition further comprises an amount of an additional factor, effective to enhance the elimination of the pathogenic cells, selected from the group consisting of a cell killing agent, a tumor penetration enhancer, a chemotherapeutic agent, an antimicrobial agent, a cytotoxic immune cell, and a compound capable of stimulating an endogenous immune response wherein the compound does not bind to the ligand-immunogen conjugate. The pharmaceutical composition contains therapeutically effective amounts of the ligand-immunogen conjugate and the therapeutic factor and the factor may comprise a cytokine such as IL-2, IL-12, or IL-15, or combinations of cytokines, including IL-2, L-12, or IL-15 and interferons such as IFN-α or IFN-γ and combinations of interferons, interleukins, and colony stimulating factors, such as GM-CSF.

The unitary daily dosage of the ligand-immunogen conjugate can vary significantly depending on the host condition, the disease state being treated, the molecular weight of the conjugate, its route of administration and tissue distribution, and the possibility of co-usage of other therapeutic treatments such as radiation therapy. The effective amount to be administered to a patient is based on body surface area, patient weight, and physician assessment of patient condition. An effective dose can range from about 1 ng/kg to about 1 mg/kg, more preferably from about 1 µg/kg to about 500 µg/kg, and most preferably from about 1 µg/kg to about 100 µg/kg.

Any effective regimen for administering the ligand-immunogen conjugate and the therapeutic factor to redirect preexisting antibodies to the tumor cells or infectious organisms or to induce a humoral response to the immunogen can be used. For example, the ligand-immunogen conjugate and therapeutic factor can be administered as single doses, or they can be divided and administered as a multiple-dose daily regimen. Further, a staggered regimen, for example, one to three days per week can be used as an alternative to daily treatment, and for the purpose of defining this invention such intermittent or staggered daily regimen is considered to be equivalent to every day treatment and within the scope of this invention. In a preferred embodiment of the invention the host is treated with multiple injections of the ligand-immunogen conjugate and the therapeutic factor to eliminate the population of pathogenic cells. In one embodiment, the host is injected multiple times (preferably about 2 up to about 50 times) with the ligand-immunogen conjugate, for example, at 12-72 hour intervals or at 48-72 hour intervals. Additional injections of the ligand-immunogen conjugate can be administered to the patient at an interval of days or months after the initial injections(s) and the additional injections prevent recurrence of disease. Alternatively, the initial injection(s) of the ligand-immunogen conjugate may prevent recurrence of disease.

The therapeutic factor may be administered to the host animal prior to, after, or at the same time as the ligand-immunogen conjugate and the therapeutic factor may be administered as part of the same composition containing the conjugate or as part of a different composition than the ligand-immunogen conjugate. Any such therapeutic composition containing the therapeutic factor at a therapeutically effective dose can be used in the present invention. Additionally, more than one type of ligand-immunogen conjugate may be used. For example, the host animal may be preimmunized with both fluorescein isothiocyanate and dinitrophenyl and subsequently treated with fluorescein isothiocyanate and dinitrophenyl linked to the same or different ligands in a co-dosing protocol. In the case of chemotherapeutic and antimicrobial agents, the therapeutic factor may be administered at a suboptimal dose along with the ligand-immunogen conjugate in a combination therapy to avoid development of resistance to the chemotherapeutic or antimicrobial agent by the host animal.

The ligand-immunogen conjugate and the therapeutic factor are preferably injected parenterally and such injections can be intraperitoneal injections, subcutaneous injections, intramuscular injections, intravenous injections or intrathecal injections. The ligand-immunogen conjugate and the therapeutic factor can also be delivered using a slow pump. Examples of parenteral dosage forms include aqueous solutions of the active agent, in an isotonic saline, 5% glucose or other well-known pharmaceutically acceptable liquid carriers such as liquid alcohols, glycols, esters, and amides. The parenteral dosage form in accordance with this invention can be in the form of a reconstitutable lyophilizate comprising the dose of ligand-immunogen conjugate and therapeutic factor. In one preferred aspect of the present embodiment, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference.

EXAMPLE 1

Effect of Folate-Fluorescein Isothiocyanate Conjugates on Survival of Mice with Lung Tumor Implants Six to eight-week old (~20-22 grams) female Balb/c mice were immunized subcutaneously at multiple sites with fluorescein isothiocyanate (FITC)-labeled bovine serum albumin (BSA) using a commercial adjuvant (e.g., Freund's adjuvant or Titer Max™-Gold). After assuring that anti-FITC antibody titers were high in all mice (as evidenced by the results of ELISA assays of serum samples of the mice), each animal was injected intraperitoneally with $5 \times 10^5$ M109 cells, a syngeneic lung cancer cell line that expresses high levels of the folate receptor. Cancer loci were then allowed to attach and grow. At 4 and 7 days post cancer cell implantation, all animals were injected intraperitoneally with either phosphate buffered saline (PBS) or a specific quantity of FITC-conjugated to folic acid via a gamma carboxyl-linked ethylene diamine bridge. The concentrations of folate-FITC injected were 0 (PBS control), 4.5, 45, 450, and 4500 nmoles/kg and 8 mice were injected per each folate-FITC concentration for a total of 40 animals injected. A series of 5 daily injections (days 8 through 12) of 5000 IU of recombinant human IL-2 were then administered to all mice in order to stimulate the immune system. The efficacy of this immunotherapy was then evaluated by monitoring survival as a function of time of folate-FITC treated mice compared to control animals. As shown in FIG. 1, median survival of mice treated with folate-FITC was dose-dependent with control mice exhibiting a median survival of 23 days post tumor implantation, and folate-FITC mice surviving increasingly longer as the dose of the conjugate was increased. As little as 45 nmoles/kg of folate-FITC was able to promote long-term survival of mice with higher doses being proportionately more effective. Although the folate-FITC was found to concentrate in tumors, some folate-FITC was present in kidney tissue (but not at comparable levels in other normal tissues). No kidney or normal organ toxicity was detected in autopsy exams by a certified veterinary pathologist.

EXAMPLE 2

Imaging of Normal Versus Tumor Tissue with Folate Conjugated to Fluorescein Isothiocyanate The procedures were similar to those described in Example 1 except that the animals were injected with 24JK-FBP tumor cells, and mice were sacrificed soon after injection with folate-FITC, and tissues were thin-sectioned and examined by FITC immunofluorescence using confocal fluorescence microscopy for localization of folate-FITC to particular tissues including tumor, kidney, liver, and muscle tissues. FIG. 2 shows phase contrast micrographs of the various tissue slices as controls along with the fluorescence micrographs. The folate-FITC was found to localize specifically in tumor tissue and in kidney proximal tubule cells where receptors for folic acid are uniquely abundant.

EXAMPLE 3

Imaging of Tumor Tissue with Folate Conjugated to Fluorescein Isothiocynate or with Phycoerythrin-Labeled Goat Anti-Mouse IgG The procedures were similar to those described in Example 2 except that M109 cells were used, and tissues were examined by FITC fluorescence (green images), and phycoerythrin (PE) fluorescence (red images). For PE fluorescence, the fluorescent label was linked to goat anti-mouse IgG antibodies for use in detecting binding of endogenous mouse anti-FITC antibodies to the folate-FITC conjugate which accumulates on the tumor cells. Folate-FITC treated and untreated tumor tissues were compared, and both types of samples were also examined by phase contrast microscopy, as described in Example 2. The FITC fluorescence demonstrates localization of folate-FITC to tumor tissues (FIG. 3). The PE fluorescence demonstrates that endogenous mouse anti-FITC antibodies bound to the folate-FITC conjugates localized to tumor cells. Other studies (not shown) demonstrate the lack of such IgG binding to normal tissues, including kidney. The absence of antibody binding to folate-FITC located in kidney tissues arises from the fact that if the folate receptor is on the apical membrane of the kidney proximal tubule cells, antibodies do not gain access to that region of the kidney. The phase contrast images (transmitted images) show the morphology of treated and untreated tumor tissues, revealing the death of cells in the treated samples.

EXAMPLE 4

Effect of Folate Fluorescein Isothiocynate Conjugates on Growth of Solid Tumors

Figure 4:
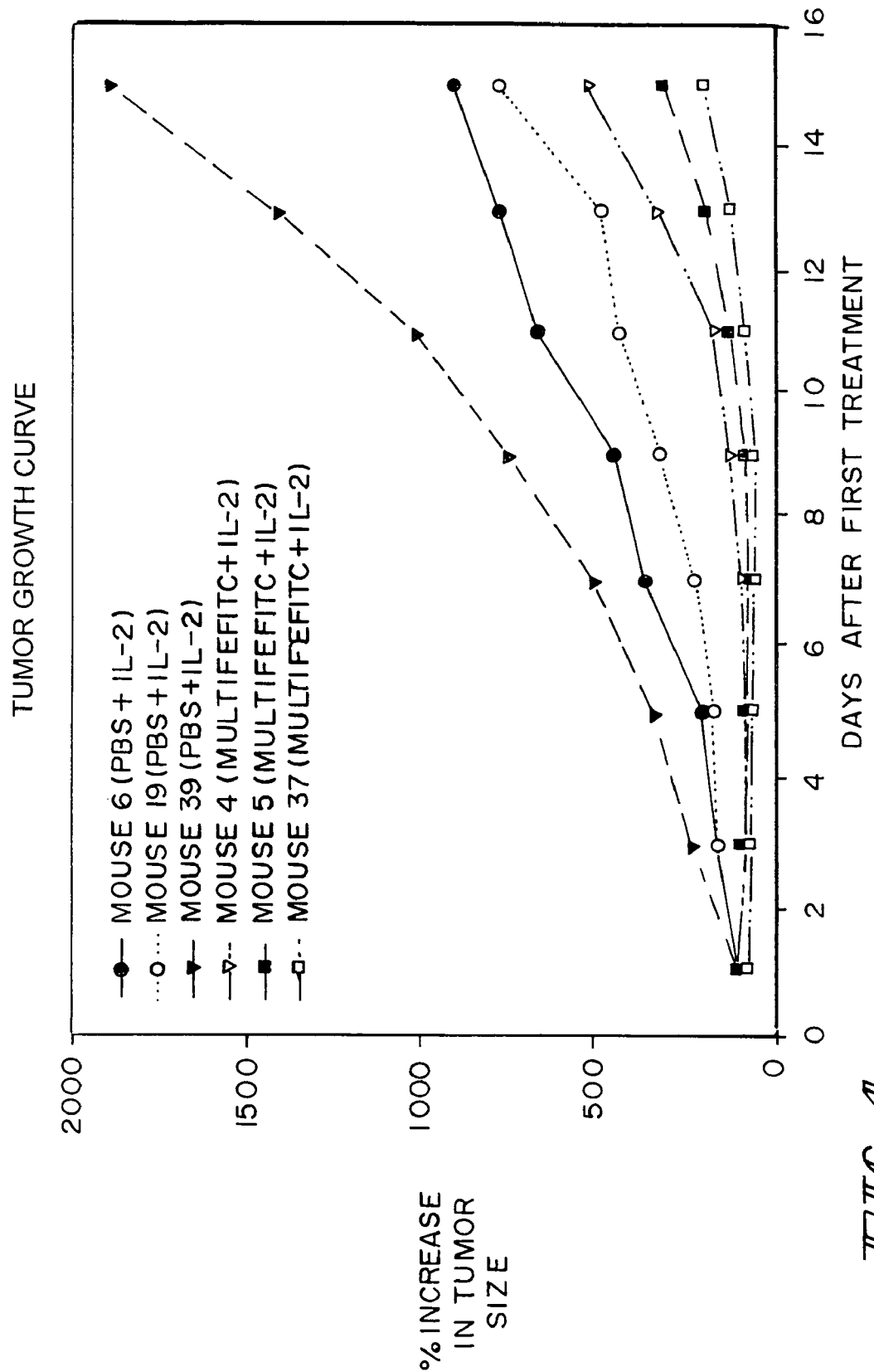
FIG. 4 shows the effect of folate-targeted immunotherapy on the growth of solid tumors.

The procedures were similar to those described in Example 1 except that each animal was injected subcutaneously in the shoulder with $1 \times 10^6$ M109 cells (day 0) following prior immunization with FITC. The immunizations with folate-FITC after tumor cell implantation consisted of 1500 nmol/kg of folate-FITC given in 6 intraperitoneal doses at 48 hour intervals (days 7, 9, 11, 13, 15, and 17). The resulting solid shoulder tumors were measured and the percent increase in tumor size was determined. The tumor growth curves depicted in FIG. 4 show that the growth of solid tumors was significantly inhibited when animals were treated with folate-FITC in combination with IL-2.

EXAMPLE 5

Effect of Treatment with Combinations of Cytokines

Figure 5:
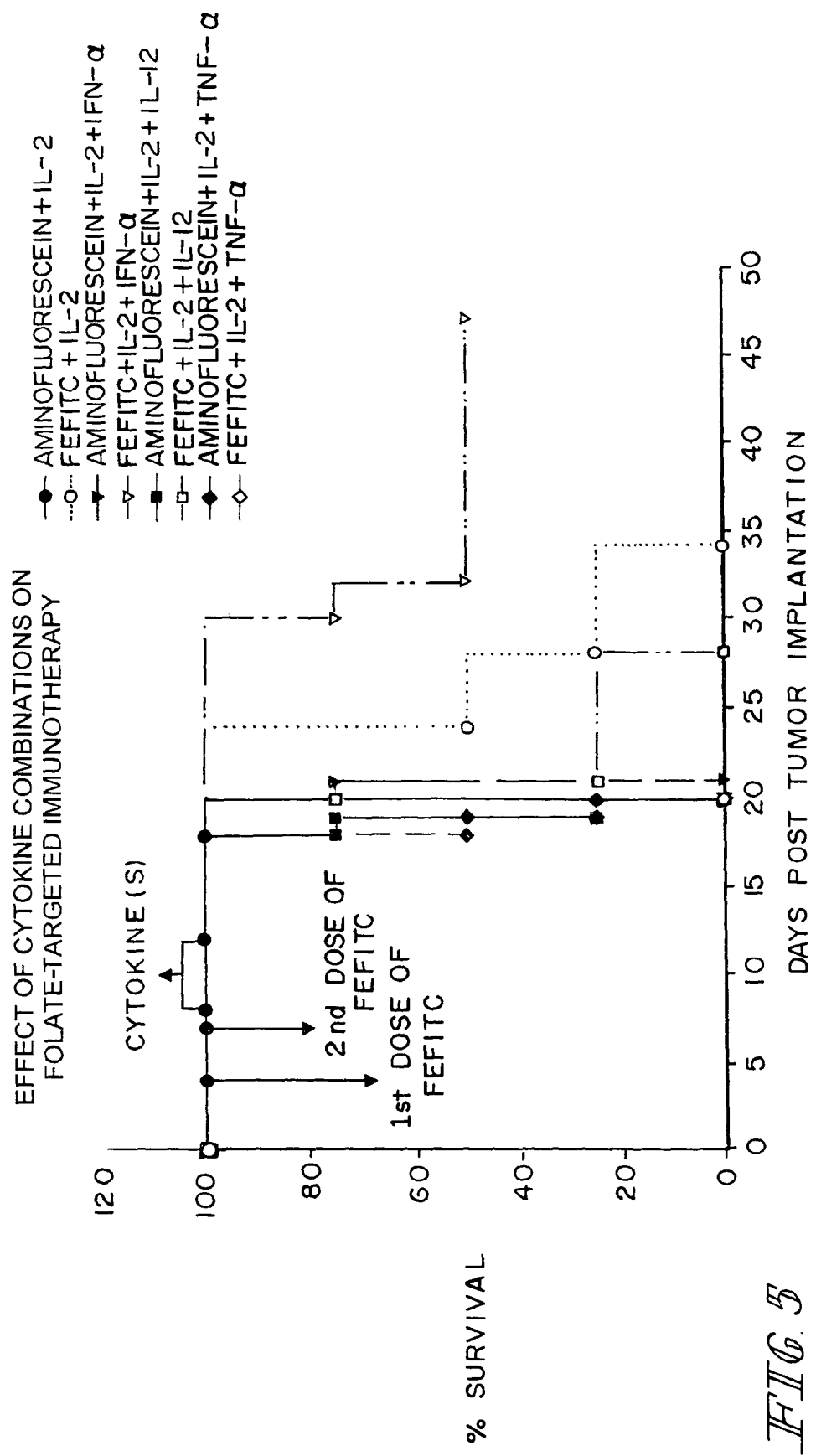
FIG. 5 shows the effect of cytokines on folate-targeted immunotherapy.

The procedures were similar to those described in Example 1 except that the animals were treated with 5 daily injections (days 8 through 12) of 5000 IU of recombinant human IL-2 along with either IFN-α (5 daily injections at $2.5 \times 10^4$ U/day), IL-12 (5 daily injections at 0.5 µg/day), or TNF-α (3 injections at days 8, 10, and 12 at 2 µg/day) subsequent to injection with 2 doses of 1500 nmol/kg of folate-FITC or aminofluorescein on days 4 and 7 after tumor cell implantation. Furthermore, in an effort to reduce the time required to obtain long-term survival data, the tumor cells were implanted intraperitoneally close to the liver. Therefore, the lifespan of tumor-bearing mice was generally shortened as compared to that shown in Example 1. The results shown in FIG. 5 demonstrate that IL-2 alone was more effective at promoting long term survival of animals than was combination treatment with IL-2 and IL-12 or with IL-2 and TNF-α. In contrast, combination treatment with IL-2 and IFN-α was more effective at promoting long term survival than was IL-2 alone. Aminofluorescein was injected along with the various cytokine combinations as a control because this compound is not linked to folate and will not retarget anti-fluorescein antibodies to tumor cells.

EXAMPLE 6

Effect of Multiple Injections with Folate Fluorescein Isothiocynate Conjugates

Figure 6:
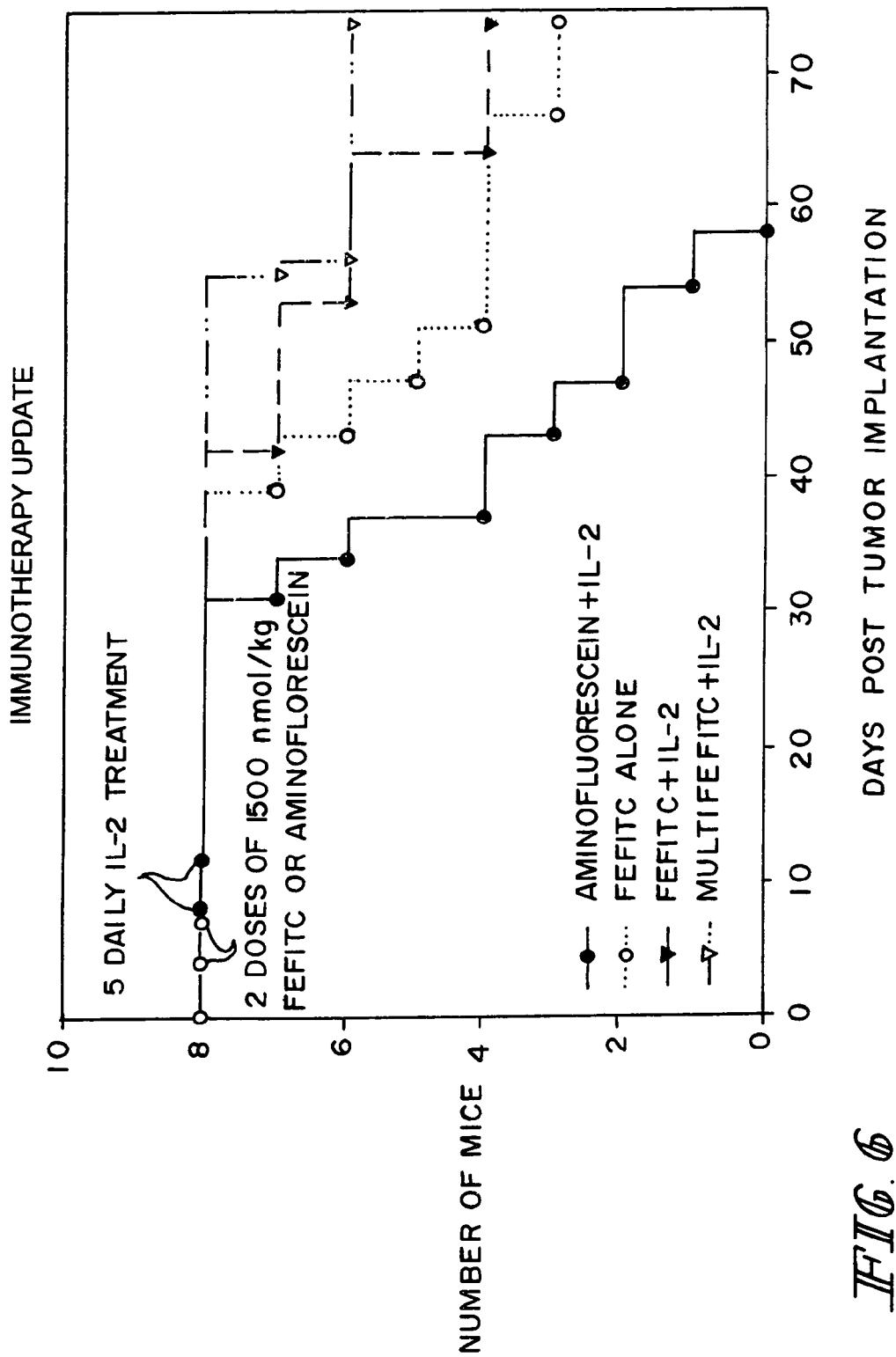
FIG. 6 shows the effect of multiple injections of folate conjugates on long-term survival of mice.

The procedures were similar to those described in Example 1 except that the animals were injected intraperitoneally at 48 hour intervals with 6 daily injections (days 7, 9, 11, 13, 15, and 17 after tumor cell implantation) of 1500 nmol/kg of folate-FITC. The results show (FIG. 6) that multiple injections with folate-FITC improved long term survival of animals treated with folate-FITC and IL-2 as compared to 2 injections of folate-FITC given at days 4 and 7 after tumor cell implantation.

EXAMPLE 7

Synergistic Effect of Folate Fluorescein Isothiocyanate Conjugates and IL-2

Figure 7:
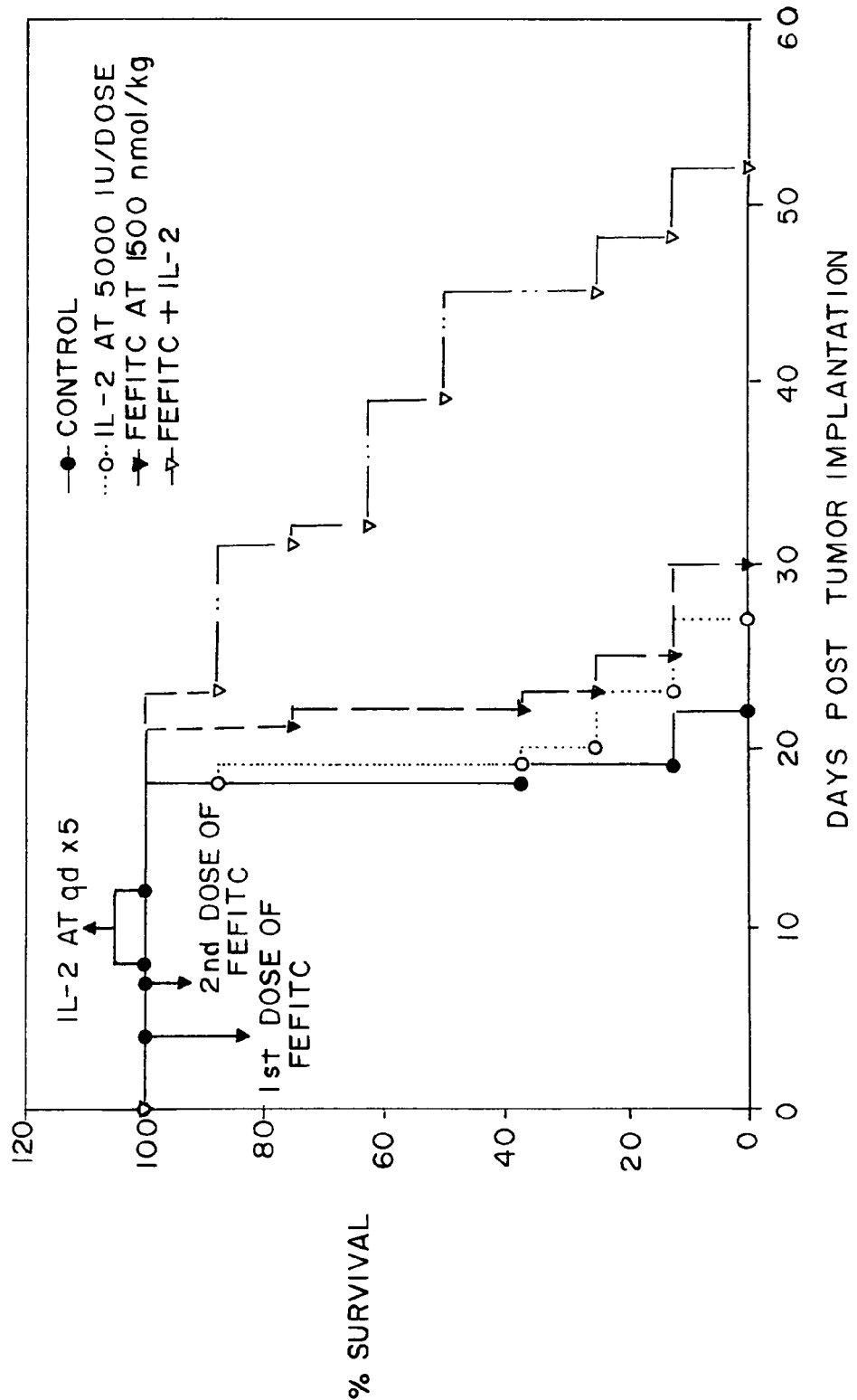
FIG. 7 shows the synergistic effect of folate conjugates and cytokines on long-term survival of mice.

The procedures were similar to those described in Example 1 except that the animals were injected with 1500 nmoles/kg of folate-FITC and some animals were treated with either folate-FITC or IL-2 alone. Furthermore, the tumor cells were implanted intraperitoneally as described in Example 5. This experiment (see FIG. 7) was performed to determine whether folate-FITC and IL-2 act synergistically to promote long-term survival of tumor-bearing mice. Median survival times for the control group (n=8), and the groups (n=8) treated with IL-2, folate-FITC, or folate-FITC+IL-2 were 18, 19, 22, and 42 days, respectively. The results shown in FIG. 7 demonstrate that the capacity of folate-FITC and IL-2 to promote long-term survival of tumor-bearing mice is strongly synergistic with low-dose IL-2 alone having a negligible effect on the survival of the mice in the absence of folate-FITC and with folate-FITC having only a minor effect.

EXAMPLE 8

NK Cell Involvement in the Synergistic Effect of Folate Fluorescein Isothiocyanate Conjugates and IL-2

Figure 8:
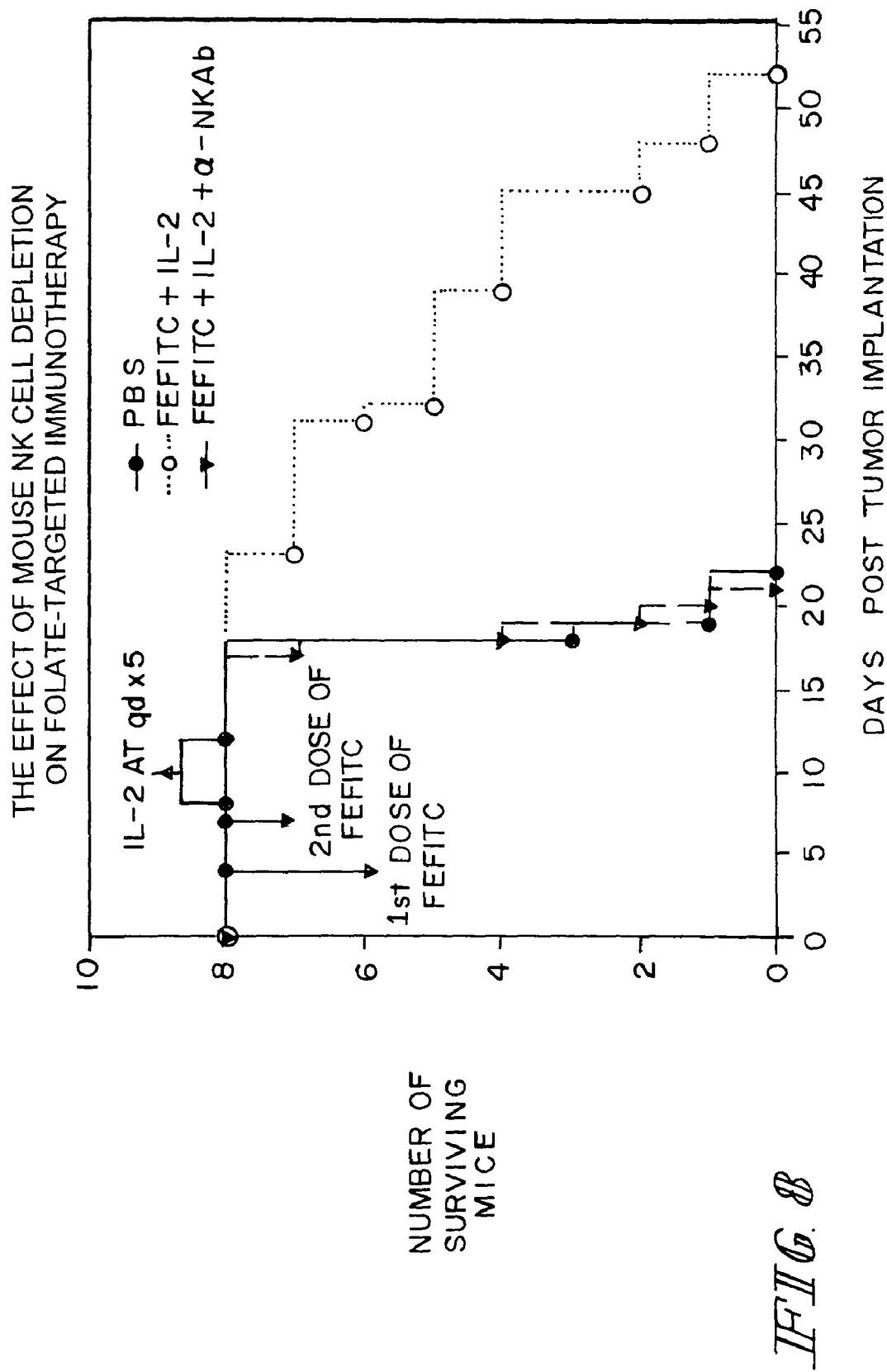
FIG. 8 shows the effect of mouse NK cell depletion on folate-targeted immunotherapy.

The procedures were similar to those described in Example 7 except that one group of animals was treated with polyclonal rabbit anti-mouse NK cell antibodies (anti-asialo GM1; Wako Pure Chemical Industries, Ltd., Richmond, Va.) in combination with folate-FITC and IL-2. Each mouse was injected with 0.2 ml of a 1:10 dilution of the antibody stock solution on days 1, 4, 9, and 14 after tumor implantation to achieve NK cell depletion. Median survival times for the control group and the groups treated with folate-FITC+IL-2 or folate-FITC+IL-2+α-NK Ab were 18, 42, and 18.5 days, respectively. The results shown in FIG. 8 demonstrate that NK cells mediate the synergistic enhancement of long-term survival of tumor-bearing mice caused by combination treatment with folate-FITC and IL-2.

EXAMPLE 9

Development of Cellular Immunity Against M109 Tumor Cells

The procedures were similar to those described in Example 1 except that the tumor cells were implanted intraperitoneally in the position described in Example 5, and the animals were injected with PBS (control) or were co-injected with folate-FITC (1500 nmoles/kg), IL-2 (250,000 IU/dose), and IFN-α (25,000 U/dose) on days 7, 8, 9, 11, and 14 after tumor cell implantation. Additionally, the animals were challenged by injection of $5 \times 10^5$ M109 cells on day 62 after initial tumor cell implantation, by injection of $1.5 \times 10^6$ M109 cells on day 96 after initial tumor cell implantation, or by injection of $2.5 \times 10^5$ Line 1 cells (a Balb/c spontaneous lung carcinoma) on day 127 after initial tumor cell implantation.

Figure 9:
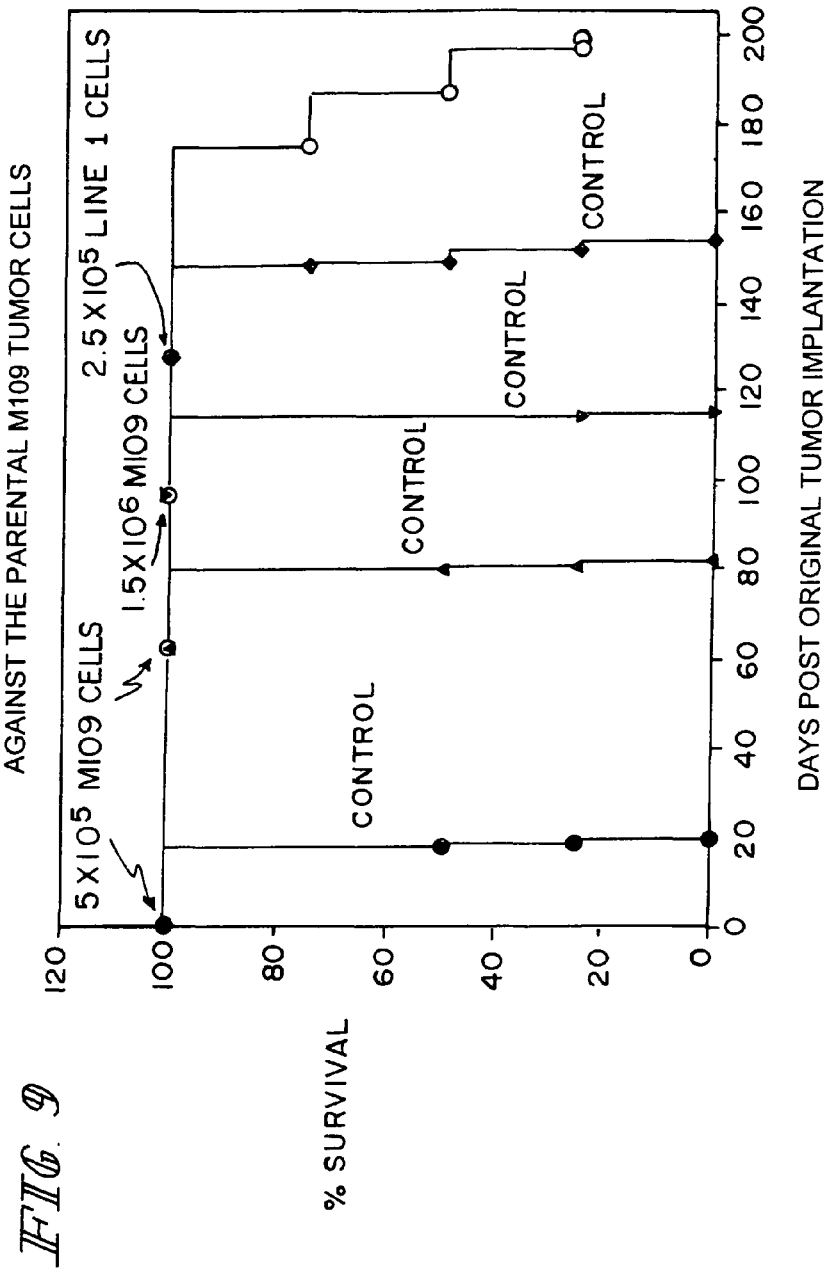
FIG. 9 shows development of cellular immunity against parental M109 cells.

As shown in FIG. 9, the median survival time of control mice injected with $5 \times 10^5$ M109 cells was 18.5 days. The median survival time of control mice injected with $1.5 \times 10^6$ M109 cells was 18 days. The median survival time of control mice injected with $2.5 \times 10^5$ Line 1 cells was 23.5 days. The median survival time of mice injected with $5 \times 10^5$ M109 cells treated with folate-FITC in combination with IL-2 and IFN-α, challenged on day 62 with $5 \times 10^5$ M109 cells, challenged on day 96 with $1.5 \times 10^6$ M109 cells, and challenged on day 127 with $2.5 \times 10^5$ Line 1 cells was greater than 192 days.

The results shown in FIG. 9 demonstrate the development of a long-lasting, cell-type specific cellular immunity in animals treated with folate-FITC in combination with IL-2 and IFN-α. This long-lasting immunity protected the animals implanted with M109 cells and receiving folate-targeted immunotherapy from the recurrence of disease upon challenge by a subsequent injection with M109 cells. The survival time in these animals after the final challenge with Line 1 cells may be due to the presence of folate receptors on Line 1 cells at lower levels than on M109 cells, and on the presence of tumor antigens shared between M109 cells and Line 1 cells resulting in a M109-specific cellular immune response capable of cross-talk with Line 1 cells.

EXAMPLE 10

Figure 10:
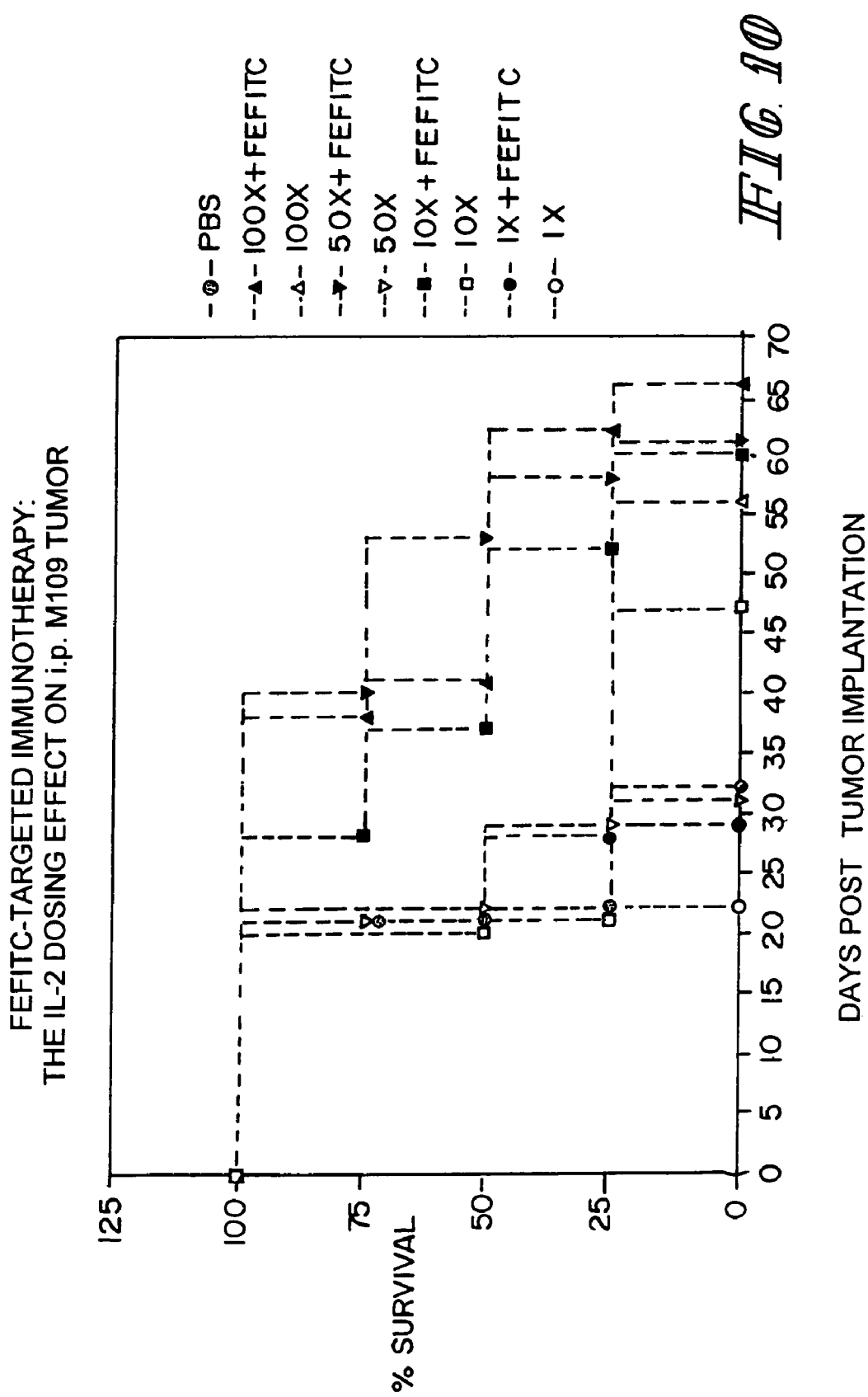
FIG. 10 shows folate-targeted immunotherapy in combination with cytokines.

Effect of IL-2 Dose on Survival of Mice Treated with Folate-Fluorescein Isothiocyanate Conjugates The procedures were similar to those described in Example 1 except that the tumor cells were implanted intraperitoneally in the position described in Example 5, and the animals were treated with PBS (control) or were co-injected with folate-FITC (1500 nmoles/kg) and IL-2 at doses of $5 \times 10^3$ IU (1×), $0.5 \times 10^5$ IU (10×), $2.5 \times 10^5$ IU (50×), or $5 \times 10^5$ IU (100×) at days 7, 8, 9, 11, and 14 after tumor cell implantation. Additionally, the animals were immunized with FITC-labeled keyhole limpit hemocyanin (KLH) rather than FITC-labeled BSA. As shown in FIG. 10, the median survival time of mice implanted with M109 cells and treated with folate-FITC increased with increasing IL-2 dose above an IL-2 dose of $5\times10^3$ IU. In contrast, no substantial difference was seen between the median survival times of control mice (mice injected with M109 cells and treated with PBS) and mice treated with IL-2 alone.

EXAMPLE 11

IFN-α Enhancement of Survival of Mice Treated with Folate-Fluorescein Isothiocyanate Conjugates and IL-2

Figure 11:
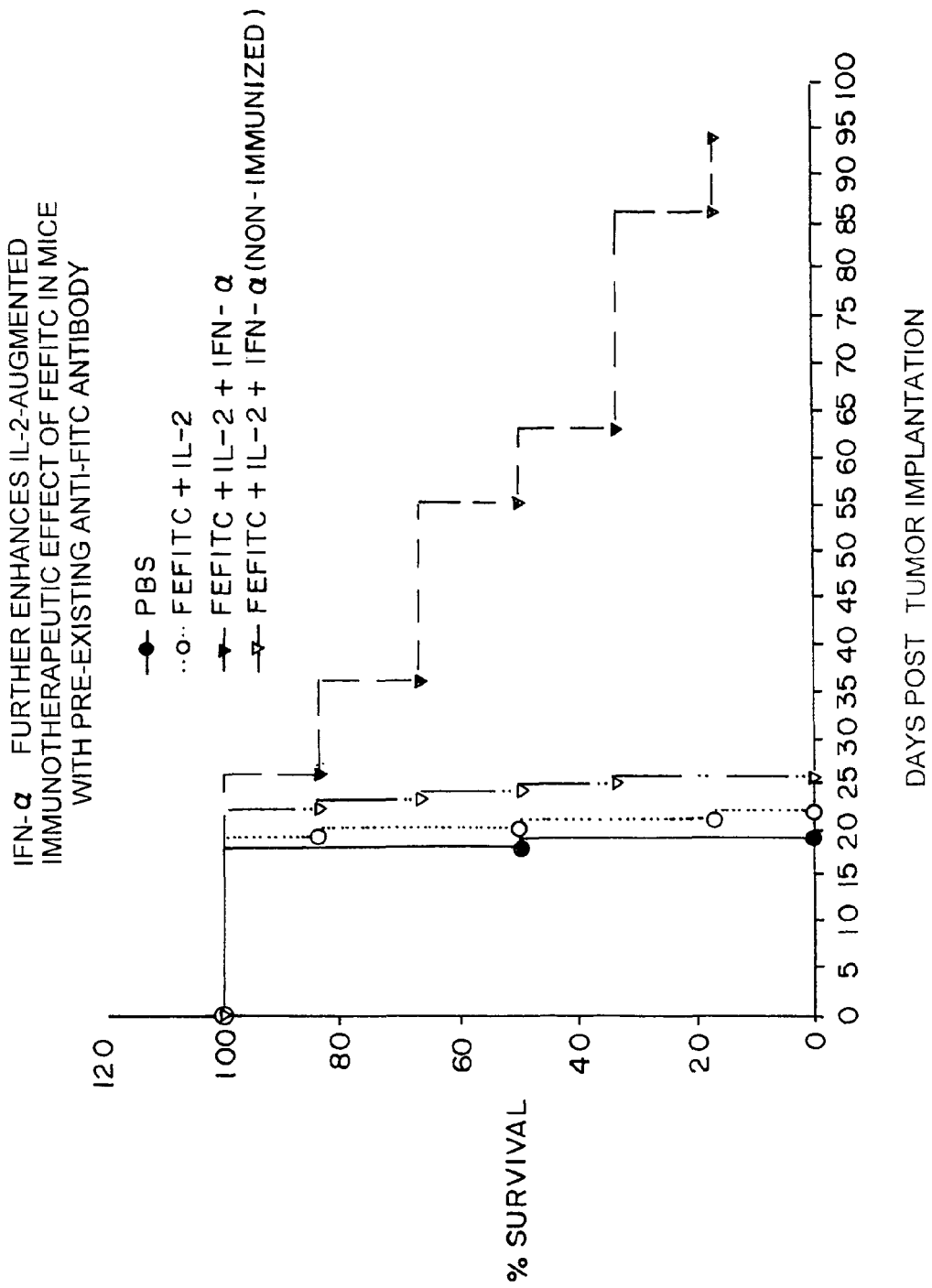
FIG. 11 shows the effect of folate-targeted immunotherapy in combination with multiple cytokines.

The procedures were similar to those described in Example 1 except that the tumor cells were implanted intraperitoneally in the position described in Example 5, and the animals were treated with PBS (control) or were co-injected with folate-FITC (1500 nmoles/kg) and IL-2 (5000 IU/dose) or folate-FITC (1500 nmoles/kg), IL-2 (5000 IU/dose), and IFN-α (25,000 U/dose) at days 7, 8, 9, 11, and 14 after tumor cell implantation. An additional group of mice were co-injected with folate-FITC, IL-2, and IFN-α, but the animals were not preimmunized with BSA-FITC. FIG. 11 shows that the median survival time for control mice treated with PBS was 18.5 days, the median survival time for mice co-injected with folate-FITC and IL-2 was 20.5 days, the median survival time for mice co-injected with folate-FITC, IL-2, and IFN-α was greater than 60 days, and the median survival time for mice co-injected with folate-FITC, IL-2, and IFN-α, but not preimmunized was 24.3 days. The median survival time for mice injected with folate-FITC and IL-2 was not substantially different than for control mice because the mice were injected with 5000 IU of IL-2, and, as described in Example 10, IL-2 doses of above 5000 IU are required to increase the median survival time in mice treated with folate-FITC using the regimen of days 7, 8, 9, 11, and 14. The results shown in FIG. 11 demonstrate that IFN-α further enhances the increase in median survival time that occurs as a result of treatment of mice implanted with tumor cells with folate-FITC and IL-2.

EXAMPLE 12

Effect of Depletion of $CD8^+$ T Cells on Folate-Targeted Immunotherapy

Figure 12:
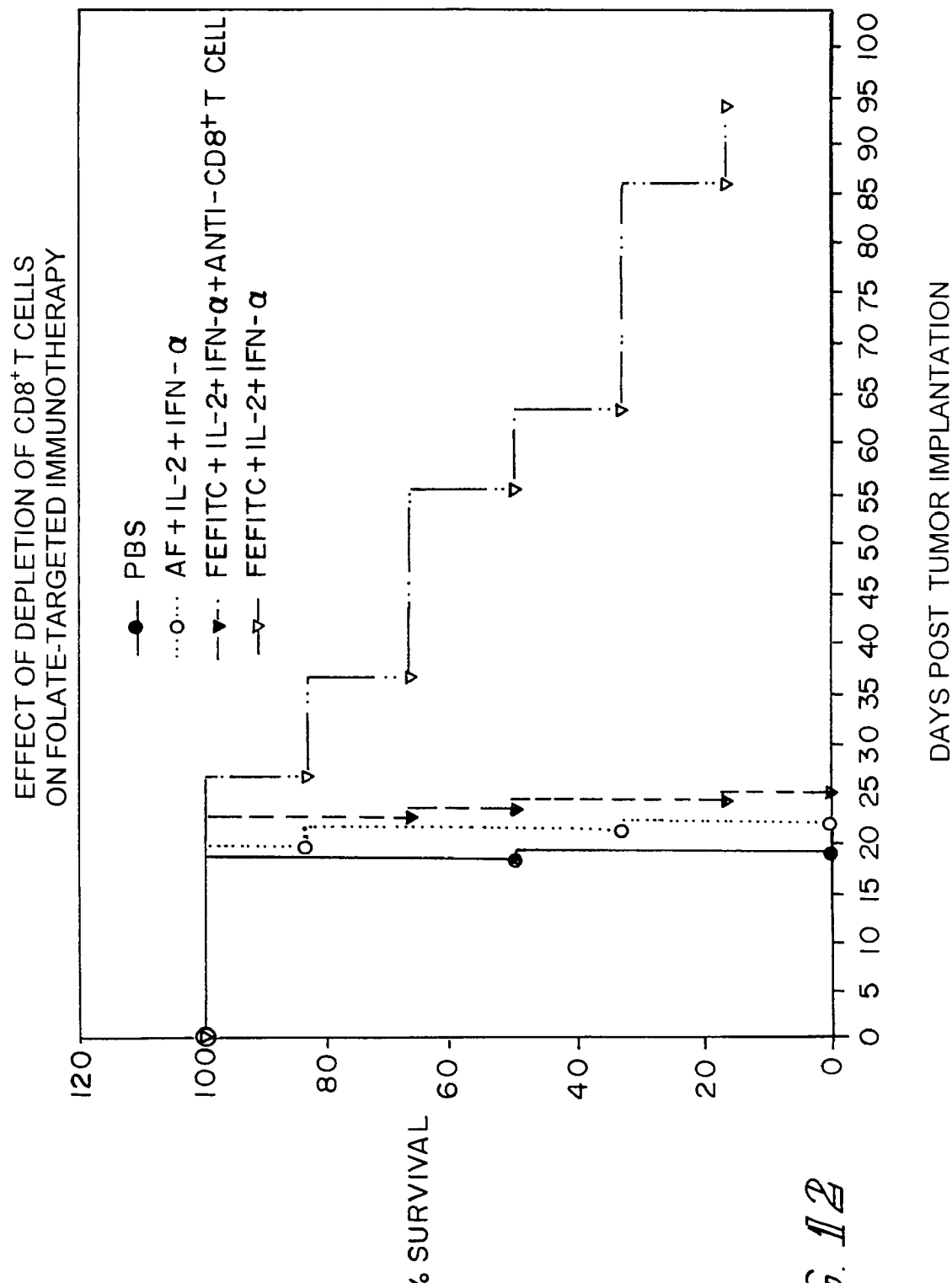
FIG. 12 shows the effect of depletion of $CD8^+$ cells on folate-targeted immunotherapy.

The procedures were similar to those described in Example 1 except that the tumor cells were implanted intraperitoneally in the position described in Example 5, and the animals were injected with PBS (control) or were co-injected with folate-FITC (1500 nmoles/kg), IL-2 (5000 IU/dose), and IFN-α (25,000 U/dose) on days 7, 8, 9, 11, and 14 after tumor cell implantation. Additional groups of mice were co-injected with aminofluorescein (1500 nmoles/kg), IL-2, and IFN-α or with folate-FITC, IL-2, IFN-α, and anti-$CD8^+$ T cell antibody (in the form of ascites and administered on days 2, 3, 7, 11, and 15). As shown in FIG. 12, the anti-$CD8^+$ T cell antibody inhibits the increase in mean survival time in mice treated with folate-FITC, IL-2, and IFN-α indicating that $CD8^+$ T cells play a role in the activation of the cellular immune response by folate-targeted immunotherapy. Aminofluorescein was injected along with the IL-2, IFN-α cytokine combination as a control because this compound is not linked to folate and will not retarget anti-fluorescein antibodies to tumor cells. FIG. 12 shows that aminofluorescein along with IL-2 and IFN-α is much less effective than folate-FITC, IL-2, and IFN-α at increasing the median survival time of mice implanted with M109 cells.

EXAMPLE 13

Augmentary Effect of GM-CSF on Folate-Targeted Immunotherapy Enhanced by IL-2 and IFN-α

Figure 13:
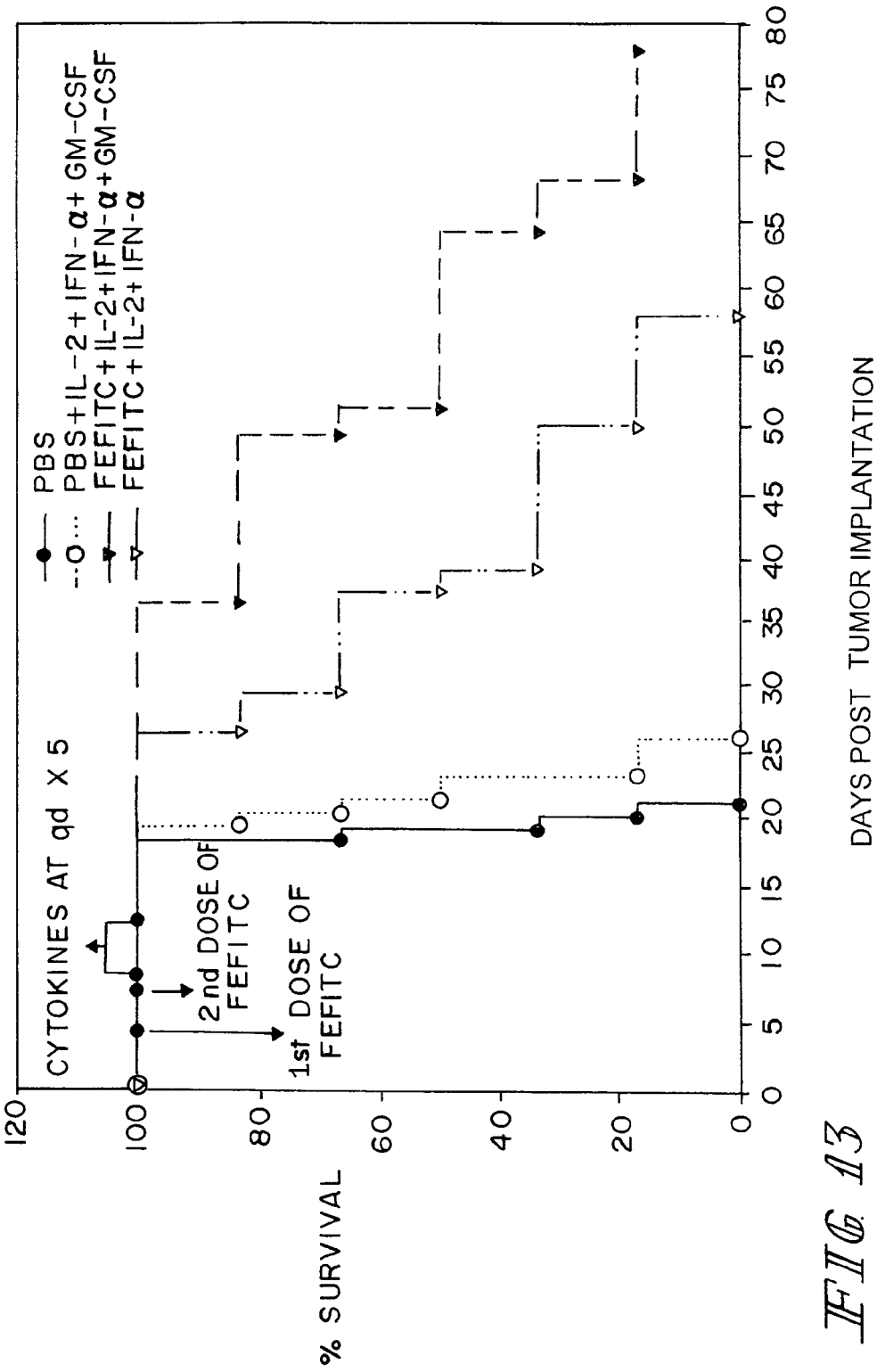
FIG. 13 shows the effect of folate-targeted immunotherapy in combination with multiple cytokines.

The procedures were similar to those described in Example 1 except that the tumor cells were implanted intraperitoneally in the position described in Example 5. Additionally, as indicated in FIG. 13, the animals were injected with multiple cytokines including IL-2 (5000 IU/dose), IFN-α (25,000 U/dose), and GM-CSF (3000 U/dose). The cytokines were co-injected in a series of 5 daily injections on days 8 to 12 after M109 cell implantation which was subsequent to injection with 2 doses of 1500 nmoles/kg of folate-FITC on days 4 and 7. The results depicted in FIG. 13 show that the median survival time for mice treated with PBS was 19 days, the median survival time for mice injected with IL-2, IFN-α, and GM-CSF without folate-FITC was 22 days, the median survival time for mice injected with folate-FITC, IL-2, and IFN-α was 38 days, and the median survival time for mice injected with folate-FITC, IL-2, IFN-α, and GM-CSF was greater than 57.5 days. The results demonstrate that GM-CSF further augments folate-targeted tumor cell killing in mice also treated with IL-2 and IFN-α. The median survival time for mice injected with PBS, IL-2, IFN-α, and GM-CSF was not significantly different than for control mice indicating the importance of targeting a tumor-specific immune response by using folate-FITC.

EXAMPLE 14

Figure 14:
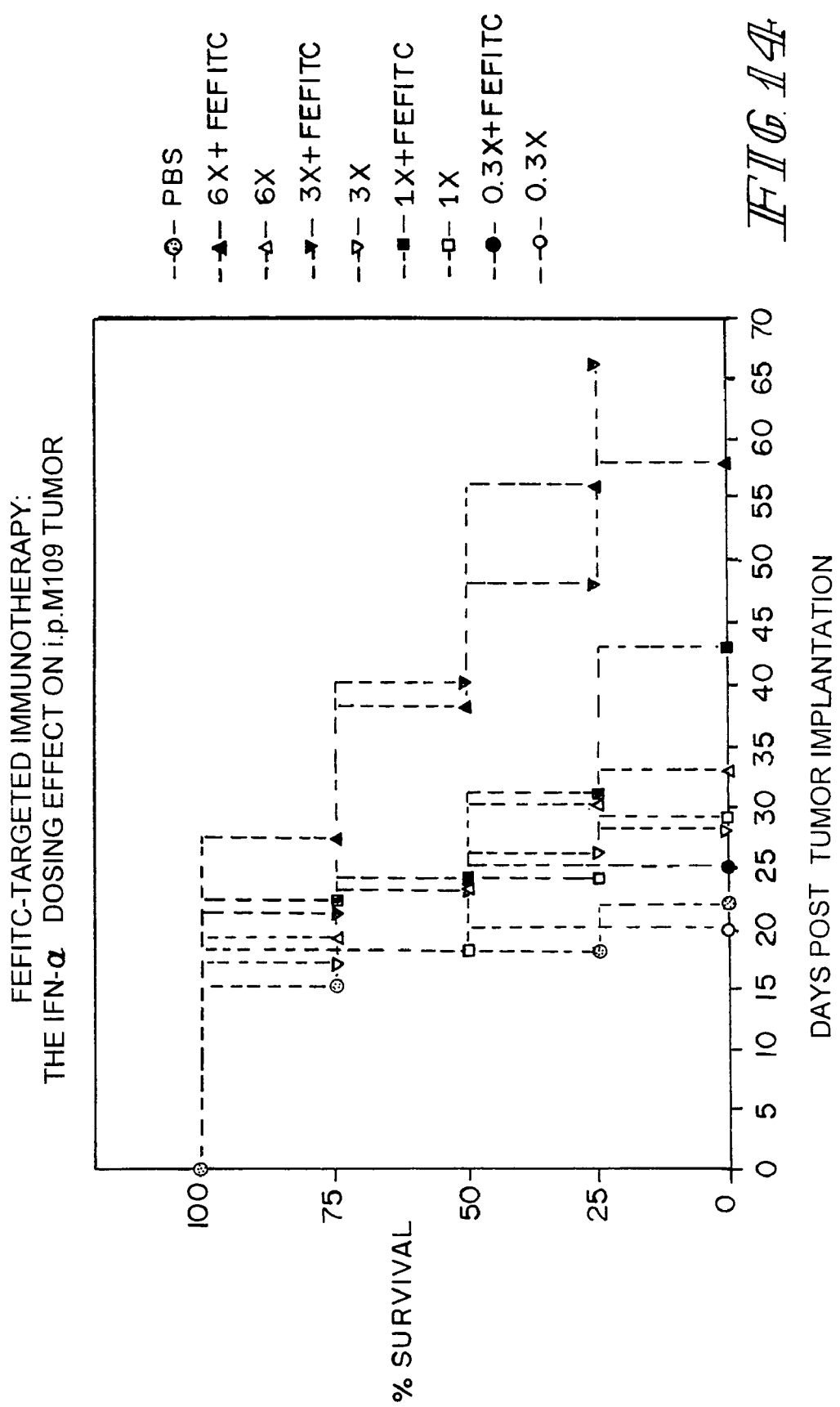
FIG. 14 shows folate-targeted immunotherapy in combination with IFN-α.

Effect of IFN-α Dose on Survival of Mice Treated with Folate-Fluorescein Isothiocyanate Conjugates The procedures were similar to those described in Example 1 except that the tumor cells were implanted intraperitoneally in the position described in Example 5, and the animals were treated with PBS (control) or were co-injected with folate-FITC (1500 nmoles/kg) and IFN-α at doses of $1.5\times10^5$ IU/dose (6×), $7.5\times10^4$ IU/dose (3×), $2.5\times10^4$ IU/dose (1×), and $7.5\times10^3$ IU/dose (0.3×). Additionally, the animals were immunized with FITC-labeled keyhole limpit hemocyanin (KLH) rather than FITC-labeled BSA, and the animals were injected with folate-FITC and IFN-α on days 7, 8, 9, 11, and 14 after tumor cell implantation. As shown in FIG. 14, the median survival time of mice implanted with M109 cells and treated with folate-FITC increased with increasing IFN-α dose above an IFN-α dose of $0.8\times10^{10}$ IU/dose.

EXAMPLE 15

Effect of Dinitrophenyl as the Immunogen on Folate-Targeted Immunotherapy

Figure 15:
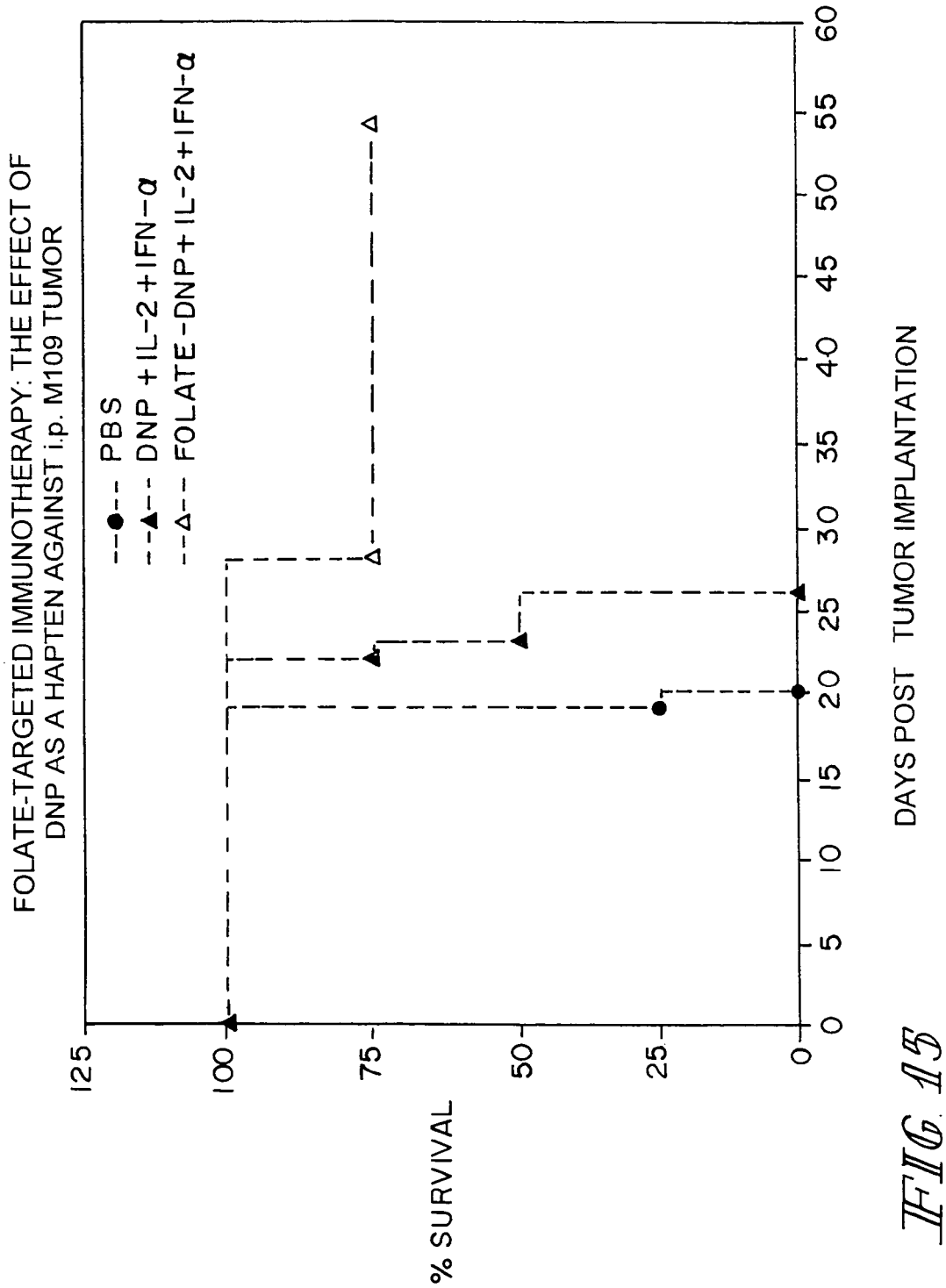
FIG. 15 shows the effect of folate-targeted immunotherapy on long-term survival of mice.

The procedures were similar to those described in Example 1 except that the tumor cells were implanted intraperitoneally in the position described in Example 5, and the animals were treated with PBS (control) or were co-injected with—dinitrophenyl (DNP) (1500 mmoles/kg), IL-2 (5000 IU/dose/day), and IFN-α ($2.5\times10^4$ units/day) or with folate-dinitrophenyl (DNP) (1500 nmoles/kg), IL-2 (5000 IU/dose/day), and IFN-α ($2.5\times10^4$ units/day) at days 7, 8, 9, 11, and 14 after tumor cell implantation. Additionally, the animals were immunized with DNP-labeled keyhole limpit hemocyanin (KLH). As shown in FIG. 15, the median survival time of mice treated with folate-DNP, IL-2, and IFN-α was increased relative to control mice (treated with PBS) or mice treated with DNP, IL-2, and IFN-α. Thus, DNP is also an effective immunogen for use in folate-targeted immunotherapy.

EXAMPLE 16

Synergistic Effect of Folate Fluorescein Isothiocyanate Conjugates and IFN-α

The procedures were similar to those described in Example 1 except that the tumor cells were implanted intraperitoneally in the position described in Example 5, and the animals were treated with PBS (control), IFN-α alone ($7.5 \times 10^4$ units/day), folate-FITC alone (1500 nmoles/kg) or were co-injected with folate-FITC (1500 nmoles/kg) and IFN-α ($7.5 \times 10^4$ units/day) at days 7, 8, 9, 11, and 14 after tumor cell implantation. Additionally, the animals (5 mice per group) were immunized with FITC-labeled keyhole limpit hemocyanin (KLH) rather than FITC-labeled BSA. As shown in FIG. 16, the median survival times for the groups treated with PBS (control), IFN-α, folate-FITC, or folate-FITC+IFN-α were 17, 17, 23, and 33 days, respectively. These results show that IFN-α, like IL-2, acts synergistically with folate-FITC to promote long-term survival of tumor-bearing mice.

EXAMPLE 17

Effect of Dinitrophenyl as the Immunogen and Cytokines at High Concentrations on Long Term Survival of Mice The procedures were similar to those described in Example 1 except that the tumor cells were implanted intraperitoneally in the position described in Example 5, and the animals were treated with PBS (control) or were co-injected with PBS, IL-2 ($2.5 \times 10^5$ units/day), and IFN-α ($7.5 \times 10^4$ units/day) or with folate-dinitrophenyl (DNP) (1500 nmoles/kg), IL-2 ($2.5 \times 10^5$ units/day), and IFN-α ($7.5 \times 10^4$ units/day) at days 7, 8, 9, 11, and 14 after tumor cell implantation. Additionally, the animals were immunized with DNP-labeled keyhole limpit hemocyanin (KLH). As shown in FIG. 17, the median survival time of mice treated with folate-DNP, IL-2, and IFN-α was increased relative to control mice (treated with PBS) or mice treated with PBS, IL-2, and IFN-α. The mice treated with folate-DNP, IL-2, and IFN-α (with IL-2 and IFN-α at concentrations of $2.5 \times 10^5$ units/day and $7.5 \times 10^4$ units/day, respectively) were completely cured.

What is claimed is:

1. A method of enhancing an endogenous immune response-mediated specific elimination of a population of cancer cells in a host animal harboring said population wherein the members of said cell population have an accessible binding site for a folate receptor-binding ligand, said method comprising the steps of administering to said host a conjugate composition comprising an immunogen conjugated to the folate receptor-binding ligand, selected from the group consisting of folate and analogs and derivatives thereof, wherein the immunogen is recognized by an endogenous or an exogenous antibody in the host or is recognized directly by an immune cell in the host, and wherein the immunogen is linked to the folate receptor binding ligand through a chemical group selected from the group consisting of a gamma carboxyl-linked ethylene diamine bridge and an alpha-carboxyl-linked ethylene diamine bridge, and wherein the immunogen is an organic molecule having a molecular weight less than 20,000 daltons; and administering to said host a compound capable of stimulating an endogenous immune response wherein the compound does not bind to the conjugate.

2. The method of claim 1 wherein the organic molecule is fluorescein or dinitrophenyl.

3. The method of claim 1 wherein the immunogen is an α-galactosyl group.

4. The method of claim 1 wherein the antibody is exogenous to said host and is administered to said host.

5. The method of claim 1 wherein the compound capable of stimulating an endogenous immune response comprises a cytokine.

6. The method of claim 5 wherein the cytokine comprises IL-2, IL-12, IL-15, or combinations thereof.

7. The method of claim 5 wherein the cytokine comprises IL-2, IL-12, IL-15, or combinations thereof, in combination with IFN-α or IFN-γ.

8. The method of claim 5 wherein the cytokine comprises IL-2, IL-12, IL-15, or combinations thereof, in combination with IFN-α or IFN-γ, or a combination thereof, and GM-CSF.

9. The method of claim 1 wherein the conjugate composition is administered in multiple injections.

10. The method of claim 1 wherein the host animal had been previously exposed naturally to the immunogen so that the host animal has a preexisting immunity to said immunogen evidenced by the presence of endogenous antibodies to the immunogen.

11. The method of claim 1 wherein the host animal had been previously exposed to the immunogen by a non-natural process resulting in priming of the host animal's immune response to said immunogen.

12. The method of claim 11 wherein the non-natural process resulting in priming of the animal's immune response is vaccination.

13. The method of claim 11 wherein the non-natural process resulting in priming of the immune response is active immunization.

14. The method of claim 1 wherein the endogenous immune response is an humoral response and the humoral response is an acquired immune response.

15. The method of claim 1 wherein the endogenous immune response is an humoral response and the humoral response is an innate immune response.

16. The method of claim 1 wherein the endogenous immune response comprises a cell-mediated immune response.

17. The method of claim 1 further comprising the step of irradiating the host animal.

18. The method of claim 1 wherein the conjugate has the formula

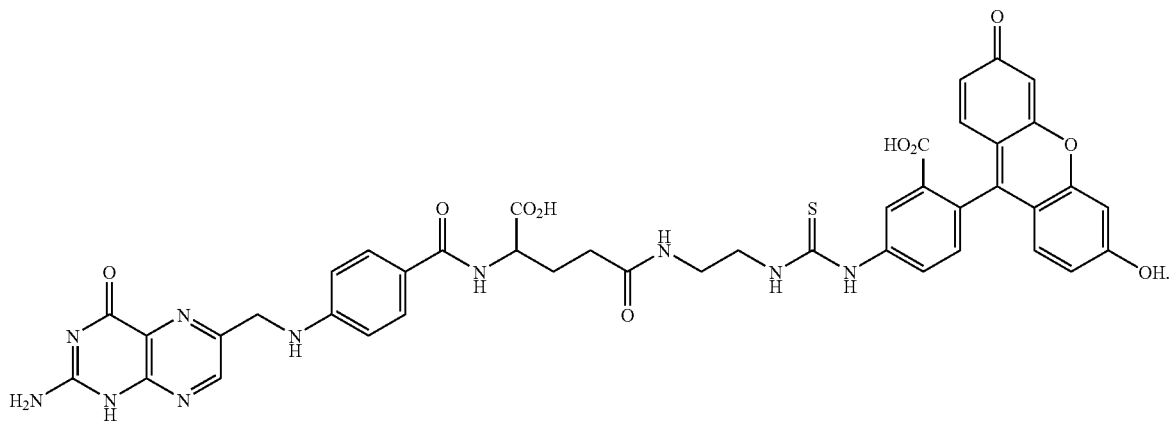

19. An injectable pharmaceutical composition comprising an immunogen conjugated to a folate receptor binding-ligand, wherein the folate receptor-binding ligand is selected from the group consisting of folate, and analogs and derivatives thereof,
wherein the folate receptor-binding ligand is linked to the immunogen only through a gamma carboxyl-linked ethylene diamine bridge,
wherein the immunogen is an organic molecule having a molecular weight less than 20,000 daltons, and
a pharmaceutically acceptable carrier therefor.

20. The pharmaceutical composition of claim 19 in a parenteral dosage form.

21. The pharmaceutical composition of claim 19 wherein the conjugate comprises folate, or an analog or derivative thereof, linked to an immunogen selected from the group consisting of an α-galactosyl group and a hapten.

22. The pharmaceutical composition of claim 21 wherein the hapten is fluorescein or dinitrophenyl.

23. The pharmaceutical composition of claim 19 wherein the conjugate has the following formula 24. The pharmaceutical composition of claim 23 wherein the conjugate is in the form of a reconstituted lyophilizate.

25. The pharmaceutical composition of claim 23 wherein the pharmaceutically acceptable carrier is selected from the group consisting of saline, a glucose solution, a liquid alcohol, a liquid glycol, a liquid ester, and a liquid amide.

26. The pharmaceutical composition of claim 19 in combination with an exogenously added compound capable of stimulating an endogenous immune response wherein the compound does not bind to the conjugate.

27. The pharmaceutical composition of claim 26 wherein the compound is an immune stimulant.

28. The pharmaceutical composition of claim 27 wherein the immune stimulant comprises a compound selected from the group consisting of IL-2, IL-12, IL-15, IFN-α, IFN-γ, and GM-CSF, or combinations thereof.

29. The pharmaceutical composition of claim 28 wherein the immune stimulant comprises a combination of IL-2 and IFN-α.

30. An injectable pharmaceutical composition comprising a compound of the formula:

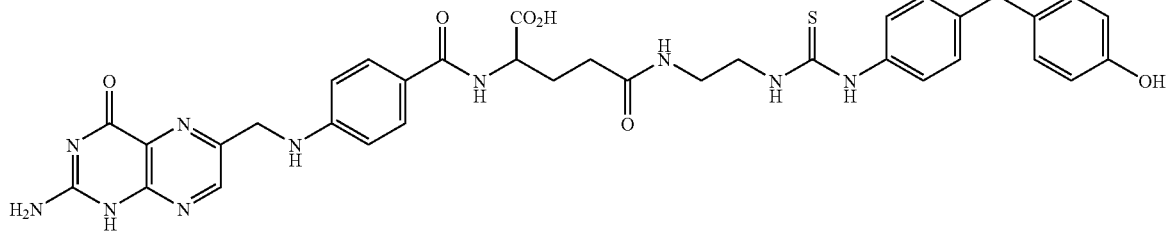

or pharmaceutically acceptable salts thereof.

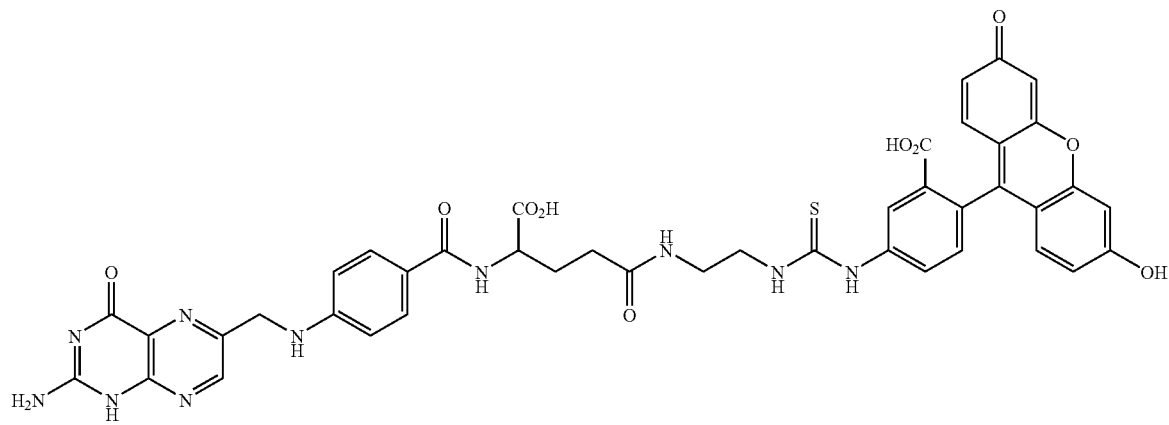

or pharmaceutically acceptable salts thereof.

31. The composition of claim 30 in combination with IL-2.

32. The composition of claim 30 in combination with IFN-α.

33. The composition of claim 30 in combination with IL-2 and IFN-α.

34. A kit comprising the composition of claim 30.

35. An injectable pharmaceutical composition comprising an immunogen conjugated to a folate receptor binding-ligand, wherein the folate receptor-binding ligand is selected from the group consisting of folate, and analogs and derivatives thereof,
   wherein the folate receptor-binding ligand is linked to the immunogen only through an α-carboxyl-linked ethylene diamine bridge,
   wherein the immunogen is an organic molecule having a molecular weight less than 20,000 daltons, and
   a pharmaceutically acceptable carrier therefor.

36. A composition comprising a compound of the formula:

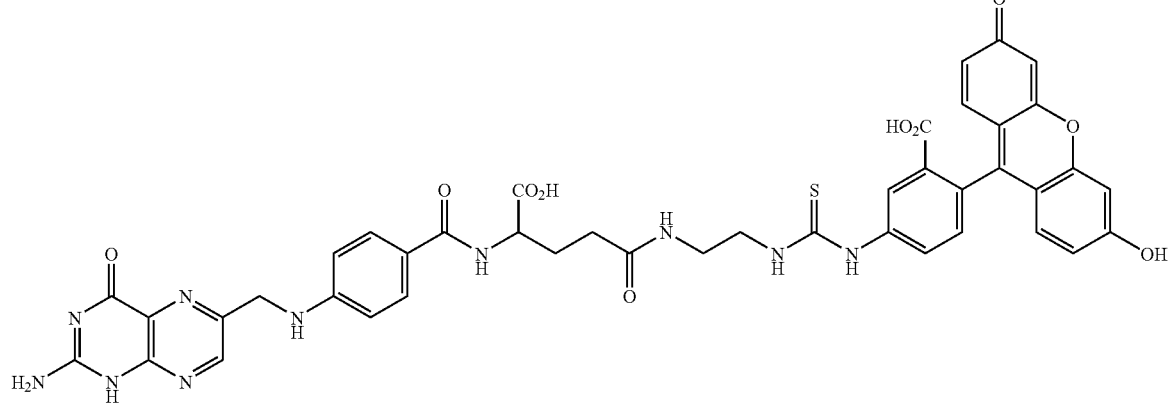

and a pharmaceutically acceptable carrier therefor.

* * * * *